(12) United States Patent
Sekiguchi et al.

(10) Patent No.: US 12,209,227 B2
(45) Date of Patent: *Jan. 28, 2025

(54) DOCOSAHEXAENOIC ACID-CONTAINING OIL AND METHOD FOR PRODUCING SAME

(71) Applicant: Nippon Suisan Kaisha, Ltd., Tokyo (JP)

(72) Inventors: Takayoshi Sekiguchi, Tokyo (JP); Yuji Okita, Tokyo (JP); Yumiko Nishizawa, Tokyo (JP)

(73) Assignee: NIPPON SUISAN KAISHA, LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/984,331

(22) Filed: Nov. 10, 2022

(65) Prior Publication Data

US 2023/0174890 A1 Jun. 8, 2023

Related U.S. Application Data

(63) Continuation of application No. 17/097,221, filed on Nov. 13, 2020, now Pat. No. 11,525,103, which is a continuation of application No. 15/993,827, filed on May 31, 2018, now Pat. No. 10,844,316, which is a continuation of application No. PCT/JP2016/085637, filed on Nov. 30, 2016.

(30) Foreign Application Priority Data

Dec. 1, 2015 (JP) .................................. 2015-234985

(51) Int. Cl.
| | |
|---|---|
| *C11B 1/10* | (2006.01) |
| *C12N 1/12* | (2006.01) |
| *C12P 7/6427* | (2022.01) |
| *C12P 7/6434* | (2022.01) |
| *C12P 7/6472* | (2022.01) |
| *C12R 1/89* | (2006.01) |

(52) U.S. Cl.
CPC .................. *C11B 1/10* (2013.01); *C12N 1/12* (2013.01); *C12N 1/125* (2021.05); *C12P 7/6427* (2013.01); *C12P 7/6434* (2022.01); *C12P 7/6472* (2013.01); *C12R 2001/89* (2021.05)

(58) Field of Classification Search
CPC ................ C11B 1/10; C12N 1/00; C12N 1/12
See application file for complete search history.

(56) References Cited

U.S. PATENT DOCUMENTS

| | | | |
|---|---|---|---|
| 6,509,178 B1 | 1/2003 | Tanaka et al. | |
| 10,023,884 B2 | 7/2018 | Ujihara et al. | |
| 11,525,103 B2 * | 12/2022 | Sekiguchi | C12P 7/6434 |
| 2005/0142275 A1 | 6/2005 | Bach et al. | |
| 2010/0190220 A1 | 7/2010 | Furihata et al. | |
| 2015/0037838 A1 | 2/2015 | Romari et al. | |
| 2017/0202762 A1 | 7/2017 | Ikeda et al. | |
| 2017/0356018 A1 | 12/2017 | Sun et al. | |

FOREIGN PATENT DOCUMENTS

| | | | | |
|---|---|---|---|---|
| CN | 102888348 B | * | 12/2014 | |
| EP | 0577371 A2 | | 1/1994 | |
| EP | 2947141 A1 | * | 11/2015 | ............... C12N 1/12 |
| JP | H06-14710 A | | 1/1994 | |
| JP | H09-272892 A | | 10/1997 | |
| JP | H10-72590 A | | 3/1998 | |
| JP | 2002-345452 A | | 12/2002 | |
| JP | 2003-52357 A | | 2/2003 | |
| JP | 2005-507028 A | | 3/2005 | |
| JP | 2012-523823 A | | 10/2012 | |
| JP | 2015-509733 A | | 4/2015 | |
| JP | 2018-117619 A | | 8/2018 | |
| WO | WO-9803671 A1 | * | 1/1998 | ........... A23K 20/158 |
| WO | WO-2009/017102 A1 | | 2/2009 | |
| WO | WO-2010/118761 A1 | | 10/2010 | |
| WO | WO-2015/174427 A1 | | 11/2015 | |

OTHER PUBLICATIONS

Santagapita et al., "Differentialscanningcalorimetryevaluationofoxidationstabilityofdocosahexaenoicacidinmicroalgaecellsandtheirextracts,"InternationalJournalofFood ScienceandTechnology,2013,pp. 1729-1735,No. 48 (Year: 2013).*
Huang T. Y. et al., Bioresource Technology, vol. 123, 2012, pp. 8-14. (Year: 2012).*
Martins et al., Mar. Drugs, 2013, vol. 11, pp. 2259-2281. (Year: 2013).*
Youkang, GRAS Notice (GRN) No. 731 , 2013 (Year: 2013).*
Tetsushi Sawada, Koretaro Takahashi and Mutsuo Hatano, Nippon Suisan Gakkaishi, 58(7), 1313-1317 (1992) (Year: 1992).*
R. Schubring, "Crystallisation and Melting Behaviour of Fish Oil Measured by DSC," Journal of Thermal Analysis and Calorimetry, 2009, pp. 823-830, vol. 95, No. 3.
Patricio Santagapita et al., "Differential scanning calorimetry evaluation of oxidation stability of docosahexaenoic acid in microalgae cells and their extracts," International Journal of Food Science and Technology, 2013, pp. 1729-1735, No. 48.
Huang T. Y. et al., "A fermentation strategy for producing docosahexaeonic acid in *Aurantiochytrium limacinum* SR21 and increasing C22:6 proportions in total fatty acid", Bioresource Technology, vol. 123, Jul. 27, 2012, pp. 8-14.

(Continued)

*Primary Examiner* — Deborah D Carr
(74) *Attorney, Agent, or Firm* — BANNER & WITCOFF, LTD.

(57) ABSTRACT

Docosahexaenoic acid-containing oil containing docosahexaenoic acid in a concentration of 40 wt. % or more of the total weight of fatty acids in the oil, and having an endothermic peak temperature determined by differential scanning calorimetry (DSC) of 15° C. or lower; a biomass including the same; and a method for producing docosahexaenoic acid-containing oil including obtaining a biomass by culturing microorganisms of the genus *Aurantiochytrium* capable of producing this docosahexaenoic acid-containing oil, recovering the biomass after culture, and extracting the oil from the biomass after recovery.

17 Claims, No Drawings

(56) References Cited

OTHER PUBLICATIONS

Chen W. et al., "Physicochemical Properties and Storage Stability of Microencapsulated DHA-Rich Oil with Different Wall Materials," Applied Biochemistry and Biotechnology, Mar. 22, 2016, vol. 179, No. 7, pp. 1129-1142.
Extended European search report dated Jun. 21, 2019 issued in European patent application No. 16 870 741.2.
Martins et al., "Alternative Sources of n-3 Long-Chain Polyunsaturated Fatty Acids in Marine Microalgae," Mar. Drugs, 2013, vol. 11, pp. 2259-2281.
Youkang, GRAS Notice (GRN) No. 731, 2013.
Sawada et al., "Effect of Column Temperature on Improvement of Resolution in Separating Triglyceride Molecular Species Containing Highly Unsaturated Fatty Acids by Reverse Phase High Performance Liquid Chromatography", Nippon Suisan Gakkaishi 1992, vol. 58, No. 7, pp. 1313-1317.
M. Hayashi, Seibutsu-kogaku, "Development of food materials by using algae", 2013, vol. 91, No. 11, pp. 621-624.
Iyoda et al., "Fatty Acid Composition of Various Fish Oils," Journal of Home Economics, vol. 23, No. 7, pp. 452-459, 1972 (with English translation).
Decision of Refusal issued Mar. 8, 2022 in Japanese Patent Application No. 2017-554159 (3 pages) with an English translation (3 pages).
Nagano et al., "Optimization of Culture Conditions for Growth and Docosahexaenoic Acid Production by a Marine Thraustochytrid, *Aurantiochytrium limacinum* mh0186," Journal of Oleo Science, vol. 58, No. 12, p. 623-628, 2009, ISSN 1345-8957 print/ISSN 1347-3352.
Notification issued Aug. 16, 2022 in Japanese Patent Application No. 2017-554159 (2 pages) with an English translation (1 page).
S. Sathivel et al., "Determination of Melting Points, Specific Heat Capacity and Enthalpy of Catfish Visceral Oil During the Purification Process," Journal of the American Oil Chemists' Society 85(3), 291-296 (2008).
Y. Taoka et al., "Effects of Cold Shock Treatment on Total Lipid Content and Fatty Acid Composition of *Aurantiochytrium limacinum* strain mh0186," Journal of Oleo Science 60(5) :217-220 (2011).
K. Yasuda, "Hydrogenation of fats and oil," Lecture Course, Oil Chemistry, vol. 36, No. 1, pp. 75-76 (1987).
S. Ueno and H. Takahashi, "Phase Transition and Crystallization of Lipids," Netsu Sokutei 41(3):104-112 (2014) (with English translation).
Tokyo Medical and Dental University of Liberal Arts Department, Masaru Wada's webpage "Welcome to the world of cell biology" / "Cell membrane", URL:https://www.tmd.ac.jp/artsci/biol/textbook/celltop.htm (update: Jun. 7, 2002, search date: Nov. 6, 2024) with machine English Translation.
Fan et al., "Lipid Characterization of Mangrove Thraustochytrid—Schizochytrium mangrovei," *Journal Agricultural and Food Chemistry*, vol. 55, pp. 2906-2910, 2007.

* cited by examiner

DOCOSAHEXAENOIC ACID-CONTAINING OIL AND METHOD FOR PRODUCING SAME

CROSS REFERENCE TO RELATED APPLICATIONS

This application is a continuation application of U.S. patent application Ser. No. 17/097,221 (allowed), filed Nov. 13, 2020, which is a continuation application of U.S. patent application Ser. No. 15/993,827, filed May 31, 2018, now U.S. Pat. No. 10,844,316, which is a continuation application of International Patent Application No. PCT/JP2016/085637 filed Nov. 30, 2016, which claims the benefit of Japanese Patent Application No. 2015-234985, the full contents of all of which are hereby incorporated by reference in their entirety.

BACKGROUND

Technical Field

The present disclosure relates to a docosahexaenoic acid containing oil and a manufacturing method thereof.

Description of the Related Art

Eicosapentaenoic acid (hereinafter, also abbreviated as EPA), docosahexaenoic acid (hereinafter, also abbreviated as DHA) and the like are n-3 unsaturated fatty acids (hereinafter, n-3 PUFA) that have various physiological effects and are utilized as medicaments, health food products, food materials, and the like. Beverages obtained by adding fish oils including DHA are recognized as food for specified health uses. There is a very high demand for n-3 PUFA as a supplement inside and outside Japan. Accordingly, there has been a demand for the production of polyunsaturated fatty acids in large quantities at high purities. In order to industrially efficiently obtain DHA as one such n-3 PUFA, while techniques for concentrating DHA in DHA containing oil into a high content using distillation techniques, and the like are used, it has been proposed to obtain an oil containing high content DHA as a raw material oil prior to applying such concentration techniques.

For example, JP 2015-509733 A discloses microorganisms which yield lipids containing higher than 40% DHA in a fatty acid composition by culturing microbial strains belonging to the genus *Schizochytrium* under culture conditions in combination with predetermined lighting conditions.

JP H10-72590 A discloses that a DHA containing oil having a DHA content of higher than 40% is obtained from a specific microorganisms belonging to of the Thraustochytrium isolated as marine microorganisms.

In oil and fat for food products, the endothermic peak determined by differential scanning calorimetry (DSC) is measured as an index with respect to the behavior of crystallization (for example, JP H06-14710 A and JP 2005-507028 A).

SUMMARY

Even an oil containing high content DHA may exhibit different properties, due to the presence of saturated or unsaturated fatty acids other than DHA. For example, even in a case where an oil contains DHA at the same high content and the temperature decreases from room temperature, in accordance with the kind and concentration of other saturated or unsaturated fatty acids, the properties of the DHA containing oil at lower temperatures change or crystallization occurs, causing the oil to solidify and consequently resulting in a reduction in handleability exemplified by pipe clogging.

Even a biomass containing high content DHA may exhibit different properties, due to the presence of saturated or unsaturated fatty acids other than DHA. For example, even regarding a biomass containing an oil containing DHA at the same high content, the properties of the entire biomass change in accordance with the kind and concentration of other saturated or unsaturated fatty acids, the viscosity increases, and consequently, the handleability may be reduced such that clogging of an apparatus such as an extruder tends to occur during kneading under high pressure, and the like.

The object of the present disclosure is to provide a docosahexaenoic acid containing oil and biomass which contain a high content docosahexaenoic acid and have excellent stability at low temperatures, along with the manufacturing method thereof.

The present disclosure includes each of the following aspects.

[1] A docosahexaenoic acid containing oil, the oil including docosahexaenoic acid at a concentration of 40 wt. % or more of the total weight of fatty acid in the oil, with the endothermic peak temperature thereof determined by differential scanning calorimetry (DSC) being 15° C. or lower.

[2] The docosahexaenoic acid containing oil according to [1], wherein the endothermic peak temperature determined by differential scanning calorimetry (DSC) is 10° C. or lower.

[3] The docosahexaenoic acid containing oil according to [1] or [2], wherein the docosahexaenoic acid concentration is from 40 wt. % to 98 wt. % of the total weight of fatty acid in the oil.

[4] The docosahexaenoic acid containing oil according to any one of [1] to [3], wherein the endothermic peak temperature determined by differential scanning calorimetry (DSC) is from −50° C. to 10° C.

[5] The docosahexaenoic acid containing oil according to any one of [1] to [4], wherein the oil is a microbial oil.

[6] The docosahexaenoic acid containing oil according to [5], wherein the microbial oil is a microbial oil of at least one microorganism selected from the group consisting of Opisthokonta, Archaeplastida, Excavata, SAR, microorganisms belonging to Haptophyta and Cryptophyta not classified as the aforementioned, and bacterium.

[7] The docosahexaenoic acid containing oil according to [5], wherein the microbial oil is a microbial oil from microorganisms belonging to Stramenopiles.

[8] The docosahexaenoic acid containing oil according to [5], wherein the microbial oil is a microbial oil from microorganisms belonging to the class Labyrinthulea.

[9] The docosahexaenoic acid containing oil according to [5], wherein the microbial oil is a microbial oil from microorganisms belonging to Thraustochytrid microorganisms.

[10] The docosahexaenoic acid containing oil according to [5], wherein the microbial oil is a microbial oil from microorganisms of the genus *Aurantiochytrium*.

[11] The docosahexaenoic acid containing oil according to [5], wherein the microbial oil is a microbial oil of a docosahexaenoic acid producing mutant of *Aurantiochytrium limacinum*.

[12] The docosahexaenoic acid containing oil according to [5], wherein the microbial oil is microbial oil of the

*Aurantiochytrium limacinum* NiD2 strain (accession number FERM BP-22296), the NiD3 strain (accession number FERM BP-22297), or a microbial strain having substantially the same microbiological properties as the strain.

[13] The docosahexaenoic acid containing oil according to any one of [1] to [12], wherein the oil is a crude oil of the microbial oil.

[14] The docosahexaenoic acid containing oil according to any one of [1] to [12], wherein the oil is a refined oil of the microbial oil.

[15] A biomass of microorganisms, the biomass including the docosahexaenoic acid containing oil according to any one of [1] to [13].

[16] The biomass according to [15], wherein the accumulative amount of the docosahexaenoic acid is 18. wt % or more of the dried biomass weight per 1 liter of a culture product.

[17] The biomass according to [15] or [16], wherein the biomass is a dried biomass.

[18] Microorganisms of the genus *Aurantiochytrium* capable of producing the docosahexaenoic acid containing oil according to any one of [1] to [14].

[19] The microorganisms of the genus *Aurantiochytrium* according to [18], wherein the microorganisms are of the *Aurantiochytrium limacinum* NiD2 strain (accession number FERM BP-22296) or the NiD3 strain (accession number FERM BP-22297).

[20] The microorganisms of the genus *Aurantiochytrium* according to [19], having substantially the same microbiological properties as the NiD2 strain (accession number FERM BP-22296) or the NiD3 strain (accession number FERM BP-22297).

[21] A manufacturing method of the biomass according to any one of [15] to [17], the method including: culturing the microorganisms of the genus *Aurantiochytrium* according to any one of [18] to [20] to obtain a biomass; and recovering the cultured biomass.

[22] The manufacturing method of biomass according to [21], the method further including drying the biomass obtained after culture.

[23] A manufacturing method of docosahexaenoic acid containing oil, the method including: culturing the microorganisms of the genus *Aurantiochytrium* according to any one of [18] to [20] to obtain a biomass; recovering the cultured biomass; and extracting oil from the recovered biomass, wherein a docosahexaenoic acid containing oil comprising docosahexaenoic acid at a concentration of 40 wt. % or more of the total weight of fatty acid in the oil is obtained from the extracted oil with the endothermic peak temperature thereof determined by differential scanning calorimetry (DSC) being 15° C. or lower.

[24] The manufacturing method according to [23], wherein the obtained docosahexaenoic acid containing oil is a crude oil.

[25] The manufacturing method according to [23], the method further including refining the extracted oil.

[26] The manufacturing method according to any one of [21] to [25], wherein the microorganisms are cultured at 10° C. to 40° C.

[27] A food product, supplement, medicament, cosmetic, or animal feed containing the docosahexaenoic acid containing oil according to any one of [1] to [14] or the biomass according to any one of [15] to [17].

[28] Use of the docosahexaenoic acid containing oil according to any one of [1] to [14] or the biomass according to any one of [15] to [17] in a manufacturing method of a food product, supplement, medicament, cosmetic, or animal feed.

According to the present disclosure, a docosahexaenoic acid containing oil and a biomass which contain a high content docosahexaenoic acid and have excellent stability at low temperatures, along with the manufacturing method thereof.

DETAILED DESCRIPTION

The docosahexaenoic acid containing oil in one embodiment is an oil including docosahexaenoic acid at a concentration of 40 wt. % or more of the total weight of fatty acid in the oil with the endothermic peak temperature thereof determined by differential scanning calorimetry (DSC) being 15° C. or lower. The biomass of microorganisms in one embodiment is a biomass including this docosahexaenoic acid containing oil, and microorganisms in one embodiment are microorganisms which may produce this docosahexaenoic acid containing oil.

Even in a case where the docosahexaenoic acid containing oil in this embodiment contains a high content docosahexaenoic acid, in addition to including components other than the docosahexaenoic acid in the oil, for example, other saturated or unsaturated fatty acids, the properties tend not to change, with the speed and behavior of crystallization moderately adjusted and a tendency seen to not solidify at low temperatures. Therefore, the docosahexaenoic acid containing oil in this embodiment can have excellent stability at low temperatures, have a suitable viscosity, and exhibit smooth properties over a wide temperature range. Consequently, the docosahexaenoic acid containing oil in itself can exhibit favorable handleability, and, can eliminate the need to combine additives such as a viscosity adjustor, additionally. The biomass and dried biomass according to this embodiment retain an oil containing the docosahexaenoic acid according to this embodiment in the biomass, thereby making them favorable to efficiently obtain the docosahexaenoic acid containing oil containing high content DHA and having excellent stability at low temperatures. Low temperatures in the present specification mean room temperature, that is, a temperature of 25° C. or lower, and for example, refers to 15° C. or lower, 10° C. or lower, or 5° C. or lower, and possibly 0° C. or lower.

In the present specification, the docosahexaenoic acid containing oil according to one embodiment containing DHA at the specific concentration and having the specific endothermic peak temperature thereof determined by DSC is also simply referred to as a "high content DHA containing oil."

In the present specification, in addition to an independent step, the term "step" also refers to a step that achieves the intended object of the step even when the step cannot be clearly distinguished from other steps. In the present specification, numeric ranges indicated by "to" are ranges that include the minimum and maximum values each stated before and after "to." In the present specification, the terms "or lower" or "or less" and "lower than" or "less than" in regard to percentages mean ranges including 0% or a value undetectable by the present means, unless the lower limit is specifically stated.

In the present specification, for the case in which multiple substances corresponding to each of the components in the mixture are present, the amount of each component in the composition, unless otherwise noted, is taken to mean the total amount of these multiple substances present in the mixture. In the present specification, for the case in which multiple substances corresponding to each of the components in the mixture are present, the concentration or content (%) of each component in the composition, unless otherwise noted, is taken to mean the total concentration or content of these multiple substances present in the mixture.

In the present specification, unless otherwise noted, when a numerical range that only specifies one or more upper limit values and a numerical range that only specifies one or more lower limit values are described for an identical target, the embodiment of the present disclosure includes a numerical range having a combination of any upper limit value chosen from the one or more upper limit values and any lower limit value chosen from the one or more lower limit values.

In the present specification, the terms "oil" and "oil and fat" refer to a mixture of organic substances which is insoluble in water at room temperature and normal pressure, that is, at 25° C. at 1 atm, includes oils containing only triglycerides and also includes crude oils containing triglycerides as a main component and other lipid such as diglycerides, monoglycerides, phospholipids, cholesterol, and free fatty acids. "Oil" and "oil and fat" mean compositions containing these lipids. In the present specification, the term "crude oil" means a mixture of the abovementioned lipids and means an oil in the state obtained by extraction from an organism. In the present specification, the term "refined oil" means an oil obtained via a refining process in which a crude oil is subjected to at least one oil and fat refining step selected from the group consisting of a degumming step, deacidification step, decoloring step, and deodorizing step to remove substances such as phospholipids and sterol other than the target.

In the present specification, a "microbial oil" means an oil obtained using microbial biomass as a source. Exemplary microbial oils include oily components such as saturated or unsaturated fatty acids, phospholipids, sterols, glycerol, ceramides, sphingolipids, terpenoids, flavonoids, and tocopherols. The saturated or unsaturated fatty acid may be present as a constituent fatty acid in other oily components.

In the present specification, the term "fatty acid" not only indicates a free saturated or unsaturated fatty acid itself, but also includes fatty acids contained as constituent units in free saturated or unsaturated fatty acids, saturated or unsaturated fatty acid alkyl esters, triglycerides, diglycerides, monoglycerides, phospholipids, steryl esters, and the like, which can also be called constituent fatty acids.

In the present specification, unless otherwise noted or indicated, when a fatty acid that is present or used is mentioned, the presence or use of fatty acid containing compounds in any form is included. Exemplary forms of compounds containing fatty acids may include a free fatty acid form, fatty acid alkyl ester form, glyceryl ester form, phospholipid form, and steryl ester form. When a fatty acid is specified, one form may be present or a mixture of two or more forms may be present.

When denoting fatty acids, a numerical expression may be used, wherein the number of carbon, the number of double bonds, and the locations of double bonds are each expressed in a simplified manner using numbers and alphabets. For example, a saturated fatty acid having 20 carbons may be notated as "C20:0." A monounsaturated fatty acid having 18 carbons may be notated as "C18:1" and the like. Dihomo-γ-linolenic acid may be notated as "C20:3, n-6" and the like. Arachidonic acid may be expressed as "C20:4, n-6" and the like. Note that "n-6" is also denoted as ω-6, with this indicating that the bonding position of a first double bond is at the sixth position when the position is counted from the last carbon (ω) to the carboxy group. This method is known to those skilled in the art and those skilled in the art can easily specify fatty acids expressed in accordance with this method.

The fatty acid concentration in the present specification is determined based on the fatty acid composition unless otherwise noted. The composition of fatty acids may be determined by standard methods. Specifically, a fatty acid lower alkyl ester obtained by esterifying the oil to be measured using a lower alcohol and a catalyst is used. Next, the obtained fatty acid lower alkyl ester is analyzed as a sample using a gas chromatograph with a flame ionization detector (FID). Peaks corresponding to each of the fatty acids are identified in the obtained gas chromatography chart, with the peak area of each of the fatty acids determined using the Agilent ChemStation integration algorithm (revision C.01.03[37], Agilent Technologies). The percentage (area %) of each peak area to the total sum of the peak area of the fatty acids is the fatty acid composition. The value according to the area % obtained by the abovementioned measurement method can be used interchangeably so as to be the same as the value according to the wt. % of each fatty acid in a sample, and regarding the fatty acid composition in the present disclosure, the area % obtained by the abovementioned measurement method is defined as the notation of "wt. %". Refer to "Basic Oil Analytical Test Methods", 2013 Edition, 2.4.2.1-2013 Fatty Acid Composition (FID constant temperature gas chromatograph method) and 2.4.2.2-2013 Fatty Acid Composition (FID heating gas chromatograph method) established by the Japan Oil Chemists' Society (JOCS).

In the present specification, the term "biomass" means an aggregation or mass of cells at a certain point of time during growth in a certain region or in an ecosystem. This region or ecosystem may be a naturally present environment, for example, a water area, or may be a synthesis environment, for example, an open type or sealed type fermentation tank or bioreactor. In the present specification, a biomass obtained after a drying step is also particularly referred to as a "dried biomass."

(1) High Content DHA Containing Oil

The high content DHA containing oil includes DHA at a concentration of 40 wt. % or more of the total weight of fatty acid in the oil and the endothermic peak temperature thereof determined by differential scanning calorimetry (DSC) is 15° C. or lower.

The DHA concentration in the high content DHA containing oil can be 40 wt. % or more, 43 wt. % or more, 50 wt. % or more, 55 wt. % or more, 60 wt. % or more, 65 wt. % or more, or 70 wt. % or more of the total weight of fatty acid in the oil. The DHA concentration in the high content DHA containing oil may be 98 wt. % or less, 90 wt. % or less, or 80 wt. % or less of the total weight of fatty acid in the oil. The upper limit value and lower limit value of the DHA concentration in the high content DHA containing oil may be any of the following combinations. For example, the DHA concentration of the high content DHA containing oil may be from 40 wt. % to 98 wt. %, from 43 wt. % to 98 wt. %, from 50 wt. % to 98 wt. %, from 60 wt. % to 98 wt. %, from 65 wt. % to 98 wt. %, or from 70 wt. % to 98 wt. % of the total weight of fatty acid in the oil. As the DHA concentration in the high content DHA containing oil increases, the function of DHA in the high content DHA containing oil can be expected to be more strongly exerted.

The high content DHA containing oil can contain a fatty acid other than DHA. Hereinafter, fatty acids other than DHA contained in the high content DHA containing oil are also referred to as "low content fatty acids." The low content fatty acid may be saturated fatty acid or unsaturated fatty acid, with one or a combination of multiple kinds capable of being contained in the oil. The low content fatty acid can be less than 60 wt. %, more than 2 wt. % and less than 60 wt. %, from 5 wt. % to 50 wt. %, or from 5 wt. % to 30 wt. % of the total weight of fatty acid in the oil. The low content fatty acid concentration can be present at a higher concentration than DHA in the total concentration in a case where multiple kinds are combined, and in this case, each concentration of low content fatty acids is preferably no higher than the DHA concentration. In terms of the stability of the high content DHA containing oil at low temperatures, regarding the high content DHA containing oil, the total concentration of the low content fatty acid present in the oil is preferably no higher than the DHA concentration. In a case where the low content fatty acid is within this range, the viscosity of the DHA containing oil at low temperatures is suitable and the handleability tends not to significantly deteriorate.

Exemplary unsaturated fatty acids which may be present as the low content fatty acid may include di- or higher, preferably tri- or higher unsaturated fatty acid having 20 or more carbons. Exemplary tri- or higher unsaturated fatty acids having 20 or more carbons may include polyunsaturated fatty acids having from 20 to 22 carbons. Specific examples thereof include eicosadienoic acid (C20:2, n-9, EDA), dihomo-γ-linolenic acid (C20:3, n-6, DGLA), Mead acid (C20:3, n-9, MA), eicosatetraenoic acid (C20:4, n-3, ETA), arachidonic acid (C20:4, n-6, ARA), eicosapentaenoic acid (C20:5, n-3, EPA), docosatetraenoic acid (C22:4, n-6, DTA), docosapentaenoic acid (C22:5, n-3, $_{n-3}$DPA), docosapentaenoic acid (C22:5, n-6, $_{n-6}$DPA), and the like.

For example, the high content DHA containing oil can include $_{n-6}$DPA, for example, 5 wt. % or more or 8 wt. % or more of the total weight of fatty acid in the oil, and can be 20 wt. % or less, or 12 wt. % or less. In a case where the content of $_{n-6}$DPA in the high content DHA containing oil is within this range, the viscosity of the DHA containing oil at low temperatures tends to be suitable and the handleability tends not to significantly deteriorate.

The total concentration of the unsaturated fatty acids which may be present as these low content fatty acids can include 5 wt. % or more or 8 wt. % or more of the total weight of fatty acid in the oil, and can be 30 wt. % or less, 20 wt. % or less, or 12 wt. % or less. The high content DHA containing oil, in which the total concentration of the low content fatty acids which may be present as unsaturated fatty acids is 30 wt. % or less, can be preferably implemented for use such that DHA is desirably efficiently obtained and stability at low temperatures may be further improved.

Exemplary saturated fatty acid, which may be present as the low content fatty acid, may include saturated fatty acids having 12 or more carbons. Exemplary saturated fatty acids having 12 or more carbons may include lauric acid (C12:0), myristic acid (C14:0), palmitic acid (C16:0), stearic acid (C18:0), arachidic acid (C20:0), behenic acid (C22:0), lignoceric acid (C24:0), and the like. In a case where the concentration of these saturated fatty acids is limited to a predetermined range, the high content DHA containing oil has more favorable stability at low temperatures, with superior handleability.

The lauric acid (C12:0) concentration in the high content DHA containing oil can be 1.0 wt. % or less, 0.5 wt. % or less, 0.3 wt. % or less, or 0.1 wt. %. The concentration ratio of the lauric acid and DHA in the high content DHA containing oil, as a ratio of lauric acid/DHA, can be 0.3 or less, 0.25 or less, or 0.2 or less. The lower limit value of the content of the lauric acid in the high content DHA containing oil may be, for example, 0.05 wt. %.

The myristic acid (C14:0) concentration in the high content DHA containing oil can be 10.0 wt. % or less, 8.0 wt. % or less, 5.0 wt. % or less, 3.0 wt. % or less, or 2.5 wt. % or less. The concentration ratio of the myristic acid and DHA in the high content DHA containing oil, as a ratio of myristic acid/DHA, can be 0.3 or less, 0.2 or less, or 0.1 or less. The lower limit value of the content of the myristic acid in the high content DHA containing oil may be, for example, 0.1 wt. %.

The palmitic acid (C16:0) concentration in the high content DHA containing oil can be 40.0 wt. % or less, 35.0 wt. % or less, or 30.0 wt. % or less. The concentration ratio of the palmitic acid and DHA in the high content DHA containing oil, as a ratio of palmitic acid/DHA, can be 0.8 or less, or 0.6 or less. The lower limit value of the content of the palmitic acid in the high content DHA containing oil may be, for example, 5.0 wt. %.

The stearic acid (C18:0) concentration in the high content DHA containing oil can be 18.0 wt. % or less, 15.0 wt. % or less, 10.0 wt. % or less, 5.0 wt. % or less, 2.0 wt. % or less, or 1.5 wt. %. The concentration ratio of the stearic acid and DHA in the high content DHA containing oil, as a ratio of stearic acid/DHA, can be 0.5 or less, 0.3 or less, or 0.1 or less. The lower limit value of the content of the stearic acid in the high content DHA containing oil may be, for example, 0.3 wt. %.

In the high content DHA containing oil, the endothermic peak temperature thereof determined by DSC is 15° C. or lower. In a case where the endothermic peak temperature determined by DSC is 15° C. or lower, the high content DHA containing oil can exhibit suitable viscosity and favorable handleability. For example, in terms of the viscosity for blending the high content DHA containing oil in other compositions, it is advantageously easily blended. The endothermic peak temperature determined by DSC of the high content DHA containing oil is also referred to as the "DSC pour point" in the present specification.

The DSC pour point is measured as follows.

A measurement sample of 10 mg is weighed in a sample pan using a differential scanning calorimetry apparatus DSC 3500 Sirius (available from NETZSCH), heated at 50° C. for 5 minutes, cooled at a cooling rate of 3° C./minute from 50° C. to −60° C., and subsequently, the temperature is raised at a temperature elevation rate of 10° C./minute from −60° C. to 50° C. for measurement. The temperature at the maximum value of the endothermic peak in the obtained DSC curve is the DSC pour point (° C.).

The DSC pour point of the high content DHA containing oil may be 10° C. or lower, 5° C. or lower, 0° C. or lower, −5° C. or lower, or −10° C. or lower. While not particularly limited thereto, the lower limit value of the DSC pour point of the high content DHA containing oil can be, for example, −65° C. or −50° C. In a case where the upper limit value of the DSC pour point is lower, the stability at low temperatures tends to be superior and to be improved handleability. While not limited to any specific theory, in a case where the upper limit value of the DSC pour point is lower, the concentration of saturated fatty acids having from 12 to 20 carbons tends to be low, and consequently, handleability at low temperatures is presumably improved. The upper limit value and lower limit value of the DSC pour point of the high content DHA containing oil may be any of the following combinations. For example, they can be from −65° C. to 15° C., from −50° C. to 10° C., from −50° C. to 5° C., from −50 to 0° C., or from −50° C. to −5° C.

Regarding the high content DHA containing oil, the content of insoluble components in the oil can be 10 wt. % or less, 5 wt. % or less, or 3 wt. % or less. In a case where the insoluble components in the oil are 10 wt. % or less, the high content DHA containing oil has high clearness as well as excellent handleability. Insoluble components in high content DHA containing oil means precipitates which are produced when the high content DHA containing oil is left to stand at 25° C. for 1 hour. The amount of insoluble components in the high content DHA containing oil is measured as follows.

One thousand milligram of the high content DHA containing oil is collected in a weighed micro test tube having a capacity of 2 ml available from Eppendorf, left to stand at 25° C. for 1 hour, after which the precipitate is recovered using a trace high speed cooling centrifuge and the precipitate weight is measured using a precision balance to be calculated as wt. % in 1000 mg of the microbial oil. As the trace high speed cooling centrifuge, MX-300 available from Tomy Seiko Co., Ltd. is used.

Derivation of the high content DHA containing oil is not particularly limited as long as it has the abovementioned predetermined DSC pour point and DHA concentration. The high content DHA containing oil can be a bio-oil derived from organisms such as plants, fish, and microorganisms, and can be, for example, a microbial oil. A bio-oil means an oil obtained using a biomass originating from organisms, while a microbial oil, as described above, means an oil obtained using a biomass originating from microorganisms. The organisms providing bio-oil may be genetically modified materials.

The high content DHA containing oil can be a crude oil or a refined microbial oil. In the present specification, "a crude oil of a microbial oil" refers to a composition which is extracted from a biomass of microorganisms and does not undergo the below mentioned refining step. In the present specification, "a refined oil of microbial oil" refers to a composition obtained via a crude oil refining process in which a crude oil from microorganisms is subjected to a degumming step, deacidification step, decoloring step using an activated clay or active carbon, washing step, deodorizing step by steam distillation, and the like to remove substances such as phospholipids and sterols other than the target.

The microorganisms may be microorganisms which may produce high content DHA containing oil, with exemplary microorganisms potentially including Opisthokonta, Archaeplastida, Excavata, SAR, microorganisms belonging to Haptophyta and Cryptophyta not classified as these, and bacterium, in the classification system (Adl et. al., The Journal of Eukaryotic Microbiology. 59(5):429-493(2012)) proposed by Adl et. al. These microorganisms may be used alone or in combination of two or more thereof. That is, among these microorganisms, the microbial oil may be a microbial oil obtained from one microorganism or may be a mixture of microbial oils obtained from two or more microorganisms.

Exemplary Opisthokonta may include microorganisms belonging to fungi. Exemplary fungi may include Yeast and filamentous fungi. Exemplary Yeast may include at least one microorganism selected from the group consisting of microorganisms of the genus *Yarrowia*, microorganisms of the genus *Pichia*, microorganisms of the genus *Saccharomyces*, microorganisms of the genus *Cryptococcus*, and microorganisms of the genus *Trichospora*. Exemplary filamentous fungi may include at least one microorganism selected from the group consisting of microorganisms of the genus *Mortierella*, microorganisms of the genus *Pythium*, and microorganisms of the genus *Phytophthora*. Of these, microorganisms belonging to the genus *Mortierella* are even more preferable. Exemplary microorganisms belonging to the genus *Mortierella* include *Mortierella elongata*, *Mortierella exigua*, *Mortierella hygrophila*, and *Mortierella alpina*.

Exemplary Archaeplastida may include microorganisms of Chlorophycea. Exemplary microorganisms of Chlorophycea may include microorganisms belonging to the genera *Botryococcus, Pseudochoricystis, Scenedesmus*, and *Desmodesmus*.

Exemplary Excavata may include microorganisms of Euglenida. Exemplary microorganisms of the class Euglenida may include microorganisms belonging to the family Euglenaceae. Exemplary microorganisms belonging to the family Euglenaceae may include microorganisms belonging to the genus *Euglena*.

SAR corresponds to microorganisms of Stramenopiles, Alveolata, and Rhizaria. Exemplary Stramenopiles may include at least one microorganism selected from the group consisting of Bicosoecida, Labyrinthulea, *Blastocystis*, Actinophyida, Opalinata, Placidida, Oomycetes, Hyphochytriomycetes, Developayella, Chrysophyceae, Eustigmatophyceae, Phaeothamniophyceae, Pinguiophyceae, Raphidophyceae, Synurophyceae, Xantexyophyceae, Phaeophyceae, Schizocladiophyceae, Chrysomerophyceae, Dictyochophyceae, Bolidophiceae, Pelagophyceae, and Bacillariophyceae microorganisms. Exemplary Alveolata may include microorganisms belonging to *Ciliophora*, Apicomplexa, and Dinoflagellates. Exemplary Dinoflagellates may include microorganisms belonging to the genus *Crypthecodinium*. Exemplary microorganisms belonging to the genus *Crypthecodinium* may include *Crypthecodinium cohnii*.

Of these, microorganisms belonging to the class Labyrinthulea are preferable as microorganisms, with microorganisms belonging to Thraustochytrid particularly preferable. As microorganisms belonging to Thraustochytrid, for example, at least one microorganism selected from the group consisting of microorganisms belonging to the genera *Aplanochytrium, Japonochytrium, Labyrinthuloides, Schizocytrium, Thraustochytrium, Ulkenia, Aurantiochytrium, Oblongichytrium, Botryochytrium, Parietichytrium*, and *Sicyoidochytrium* can be preferably selected, among which microorganisms of the genus *Aurantiochytrium* are particularly preferably selected.

As microorganisms of the genus *Aurantiochytrium*, at least one selected from the group consisting of *Aurantiochytrium limacinum* and *Aurantiochytrium mangrovei* can be selected, with *Aurantiochytrium limacinum* particularly selected in terms of growth of microorganisms.

The microorganisms belonging to Haptophyta and Cryptophyta correspond to microorganisms belonging to Haptophyta and Cryptophyta which do not belong to any of Opisthokonta, Archaeplastida, Excavata, or SAR. Specific examples thereof may include the classes Haptophyceae and Cryptophyceae.

Exemplary bacteria may include microorganisms of Proteobacteria and Firmicutes. Exemplary microorganisms belonging to Proteobacteria may include *Escherichia coli*. Exemplary microorganisms belonging to Firmicutes may include *Bacillus subtilis*.

In a case where Stramenopiles are selected as microorganisms for DHA production among the abovementioned microorganisms, DHA production efficiency tends to be further improved. Moreover, marine microorganisms present in the ocean or brackish water regions among Stramenopiles have relatively high DHA production efficiency.

Among marine microorganisms, microorganisms of the genus Thraustochytrium, microorganisms of the genus *Aurantiochytrium*, microorganisms of the genus *Schizochytrium*, microorganisms of the genus *Ulkenia*, microorganisms of the genus *Crypthecodinium* among *Alveolata*, and mutants thereof tend to produce higher productivity of DHA in particular than other microorganisms. In the present specification, these microorganisms are also particularly referred to as "DHA highly productive microorganisms." Exemplary high content DHA containing oils may include a DHA highly productive microbial oil originating from DHA highly productive microorganisms, a bacterium oil originating from a bacterial biomass, a fungus oil originating from a fungus biomass, a filamentous fungus oil originating from a filamentous fungus biomass, and the like. Of these, DHA highly productive microbial oils tend to have a particularly high DHA concentration.

Because the classification of microorganisms generally has unconfirmed parts, microorganisms which may produce high content DHA containing oil can be selected based on criteria other than the abovementioned taxonomic position. Exemplary criteria other than such a taxonomic position may include morphology and fatty acid composition. In a case where microorganisms are selected based on morphology, the microorganisms have at least one flagellar basal body and include a structure for accumulating lipids represented by lipid droplets in cells, and the like. Upon selection based on the fatty acid composition, examples thereof include tri- or higher unsaturated fatty acid having 20 or more carbons. Specific examples thereof include at least one selected from the group consisting of eicosadienoic acid (C20:2, n-9, EDA), dihomo-γ-linolenic acid (C20:3, n-6, DGLA), Mead acid (C20:3, n-9, MA), eicosatetraenoic acid (C20:4, n-3, ETA), arachidonic acid (C20:4, n-6, ARA), eicosapentaenoic acid (C20:5, n-3, EPA), docosatetraenoic acid (C22:4, n-6, DTA), docosapentaenoic acid (C22:5, n-3, $_{n-3}$DPA), and docosapentaenoic acid (C22:5, n-6, $_{n-6}$DPA). Microorganisms may be selected based on both the morphology and fatty acid composition, or only one thereof.

As long as the microorganisms have the capacity to produce high content DHA containing oil, the microorganisms may be a wild strain collected under a natural environment, or may be a high content DHA containing oil producing mutant obtained by artificially or incidentally inducing mutation to the wild strain.

As a method for creating mutants, a known mutation inducing method can be used without being particularly limited. Exemplary methods for creating mutants may include processes using radiation, mutagens, and the like. In a case where the mutation inducing process is carried out using at least one of radiation or a mutagen, the process can be carried out such that the death ratio of microorganisms is 98%, 99%, or 99.9%. With the mutation inducing process using such a death ratio, microorganisms useful for obtaining the high content DHA containing oil can be frequently acquired.

In the mutation inducing method involving a process using a mutagen, the selected mutagen is added to microorganisms serving as the target to induce mutation. The application amount of the mutagen may be the application amount capable of inducing mutation and is appropriately selected in accordance with the kind of microorganisms, state of microorganisms, load on microorganisms, kind of mutagen, and the like.

While not limited thereto, exemplary selectable mutagens may include ethyl methane sulfonate (EMS), methyl methane sulfonate (MMS), N-ethyl-N-nitrosourea (ENU), triethyl melamine (TEM), N-methyl-N-nitrosourea (MNU), procarbazine, chlorambucil, cyclophosphamide, diethyl sulfate, acrylamide monomer, melphalan, nitrogen mustard, vincristine, dimethyl nitrosoamine, N-methyl-N'-nitro-nitrosoguanidine (NTG), 2-aminopurine, 7, 12 dimethyl-benz(a)anthracene (DMBA), ethylene oxide, hexamethyl phosphoramide, busulfan, diepoxy alkanes (diepoxy octane (DEO), diepoxy butane (BEB), and the like), 2-methoxy-6-chloro-9[3-(ethyl chloroethyl)aminopropylamino]acridine dihydrochloride (ICR-170), formaldehyde, and the like. At least one selected from the group consisting of these mutagens may be selected.

The state of microorganisms targeted for the process using mutagens, that is, the density, growth stage, and the like can be appropriately selected in accordance with the kind and growth state of microorganisms, and the like. The morphology of the microorganisms targeted for the process using mutagens may be a growing microbial body (vegetable cells, mycelia, and the like) or zoospores and spores. In terms of efficiently obtaining a mutant producing the high content DHA containing oil, microorganisms targeted for the process can be microorganisms forming zoospores.

In terms of acquisition efficiency, as microorganisms targeted for the mutation inducing process useful for obtaining the high content DHA containing oil, at least one microorganism selected from the group consisting of microorganisms belonging to the genera *Schizochytrium*, *Thraustochytrium*, *Aurantiochytrium*, and *Aplanochytrium* is preferable, among which microorganisms of the genus *Aurantiochytrium* are particularly preferable, and the at least one microorganism can be processed using mutagens to obtain mutants.

Microorganisms useful for obtaining the high content DHA containing oil include at least one microorganism selected from the group consisting of microorganisms belonging to the genera *Schizochytrium*, *Thraustochytrium*, *Aurantiochytrium*, and *Aplanochytrium*, among which microorganisms of the genus *Aurantiochytrium* are particularly preferable. The at least one microorganism can be processed to obtain mutants using a mutagen, for example, at least one drug selected from the group consisting of ethyl methane sulfonate (EMS), N-ethyl-N-nitrosourea (ENU), and N-methyl-N'-nitro-nitrosoguanidine (NTG), such that the death ratio of microorganisms is 98%, 99%, or 99.9% with respect to microorganisms in the growth stage forming the zoospores. These mutants may further efficiently produce the high content DHA containing oil.

Alternatively, microorganisms useful for obtaining the high content DHA containing oil include a mutant obtained from at least one microorganism selected from the group consisting of *Aurantiochytrium limacinum*, *Aurantiochytrium mangrovei*, and the like, by a treatment using a mutagen, for example, at least one drug selected from the group consisting of ethyl methane sulfonate (EMS), N-ethyl-N-nitrosourea (ENU), and N-methyl-N'-nitro-nitrosoguanidine (NTG), such that the death ratio of microorganisms is 98%, 99%, or 99.9% with respect to microorganisms in the growth stage forming the zoospores. These mutants may further efficiently produce the high content DHA containing oil.

Exemplary mutants useful for obtaining the high content DHA containing oil may include *Aurantiochytrium limacinum* NiD2 strain and NiD3 strain, as well as microbial strains having substantially the same microbiological properties as these microbial strains. *Aurantiochytrium limacinum* NiD2 strain and NiD3 strain, as well as microbial strains having substantially the same microbiological properties as these microbial strains, can stably produce the high content DHA containing oil specified in the present specification. *Aurantiochytrium limacinum* NiD2 strain and NiD3 strain, as well as the NBL-8 strain which is the parent strain thereof, were deposited by the National Institute of Technology and Evaluation Patent Organism Depositary Center (#120, 2-5-8, Kazusakamatari, Kisarazu-shi, Chiba, Japan) on Oct. 7, 2015 (NBL-8 strain: accession number FERM BP-22295, NiD2 strain: accession number FERM BP-22296, and NiD3 strain: accession number FERM BP-22297).

In a case where the high content DHA containing oil is a microbial oil, the high content DHA containing oil can include other components characteristic of the microbial oil, can exhibit a fatty acid composition characteristic of microorganisms, or can include other components characteristic of microorganisms and exhibit a peculiar fatty acid composition. Exemplary other components characteristic of the microbial oil may include phospholipids, free fatty acids, fatty acid esters, monoacyl glycerols, diacyl glycerols, triacyl glycerols, sterols and sterol esters, carotenoids, xanthophylls, ubiquinones, hydrocarbons, isoprenoid derived compounds, compounds with any of these metabolized, and the like.

Because the high content DHA containing oil as the microbial oil can be obtained without undergoing a chemical synthesis step, the organic solvent content can be low. The organic solvent in the present specification means an organic solvent other than fatty acids and means a hydrophobic or hydrophilic solvent having at least one carbon atom. Exemplary organic solvents include polar solvents, nonpolar solvents, water miscible solvents, water immiscible solvents, and combinations of at least two of the solvents. Exemplary organic solvents include substituted or unsubstituted, saturated or unsaturated aliphatic hydrocarbons, aromatic hydrocarbons, alcohols, ethers, ketones, aldehydes, carboxylic acids, esters, nitriles, amides and the like. The organic solvent may be one type of these or a combination of at least two of these.

The total content of the residual organic solvent in the high content DHA containing oil may be 5000 ppm or less, 3000 ppm or less, 2000 ppm or less, or 1000 ppm or less.

The high content DHA containing oil may have a low content of at least one selected from the group consisting of methanol, ethanol, acetone, and hexane among the organic solvents. The content of these organic solvents may each independently be 500 ppm or less, 300 ppm or less, or 200 ppm or less. For example, the entire content of methanol, ethanol, acetone, and hexane in the high content DHA containing oil may be 500 ppm or less, 300 ppm or less, or 200 ppm or less.

In a case where the high content DHA containing oil is a crude oil of a microbial oil, the DHA concentration can be 40 wt. % or more, 43 wt. % or more, 50 wt. % or more, 55 wt. % or more, 60 wt. % or more, 65 wt. % or more, or 70 wt. % or more of the total weight of fatty acid in the oil. In a case where the high content DHA containing oil is a crude oil from microorganisms, the DHA concentration may be 95 wt. % or less, 90 wt. % or less, 85 wt. % or less, or 80 wt. % or less of the total weight of fatty acid in the oil. The upper limit value and lower limit value of the DHA concentration in the high content DHA containing oil may be any of the following combinations. For example, the DHA concentration of the high content DHA containing oil can be from 40 wt. % to 95 wt. %, from 40 wt. % to 85 wt. %, from 40 wt. % to 80 wt. %, from 60 wt. % to 80 wt. %, from 70 wt. % to 85 wt. %, or from 70 wt. % to 95 wt. % of the total weight of fatty acid in the oil.

In terms of stability at low temperatures, the high content DHA containing oil may be any of the following:

a microbial oil of *Aurantiochytrium limacinum* which contains DHA at from 40 wt. % to 95 wt. % of the total weight of the fatty acid in the oil and has a DSC pour point of 10° C. or lower;

a microbial oil from microorganisms of the genus *Aurantiochytrium* which contains DHA at from 65 wt. % to 80 wt. % of the total weight of fatty acid in the oil and has a DSC pour point of 5° C. or lower;

a crude oil of a microbial oil of *Aurantiochytrium limacinum* which contains DHA at from 40 wt. % to 95 wt. % of the total weight of the fatty acid in the oil and has a DSC pour point of 10° C. or lower;

a crude oil of a microbial oil from microorganisms of the genus *Aurantiochytrium* which contains DHA at from 65 wt. % to 80 wt. % of the total weight of the fatty acid in the oil and has a DSC pour point of 5° C. or lower;

a microbial oil from microorganisms of the genus *Aurantiochytrium* which contains DHA at from 40 wt. % to 95 wt. % of the total weight of the fatty acid in the oil and has a DSC pour point from −50° C. to 10° C. or lower; and a crude oil of a microbial oil of *Aurantiochytrium limacinum* which contains DHA at from 40 wt. % to 80 wt. % of the total weight of the fatty acid in the oil and has a DSC pour point from −50° C. to 5° C. or lower.

The high content DHA containing oil may be contained in the biomass as described later. The high content DHA containing oil may be contained in specific microbial biomasses, for example, biomasses of *Aurantiochytrium limacinum* NiD2 strain (accession number FERM BP-22296), NiD3 strain (accession number FERM BP-22297), and a microbial strain having substantially the same microbiological properties as these strains.

(2) DHA Containing Biomass

The DHA containing biomass according to one embodiment of the present disclosure contains the abovementioned high content DHA containing oil, that is, an oil including DHA at a concentration of 40 wt. % or more of the total weight of fatty acid in the oil, with the endothermic peak temperature thereof determined by DSC being 15° C. or lower. In the present specification, a biomass containing the high content DHA containing oil in one embodiment of the present disclosure is also simply referred to as a "high content DHA containing biomass."

The high content DHA containing biomass can be of any morphology as long as it is an aggregate or mass of microorganisms producible the abovementioned high content DHA containing oil. For example, the high content DHA containing biomass may be an aggregate or mass of microorganisms in a culture liquid, an aggregate or mass of microorganisms after being recovered from the culture liquid, or an aggregate or mass of microorganisms undergoing a drying process after being recovered from the culture liquid. In the event of particularly indicating the high content DHA containing biomass via the drying process, it is also referred to as "a high content DHA containing dried biomass" in the present specification. The high content DHA containing dried biomass is in the dried form, allowing it to be easily handled.

In the high content DHA containing biomass or the high content DHA containing dried biomass, the high content DHA containing oil may be present in individual cells which make up the biomass and may be released outside the cells in a case where it can be recovered from the cultured biomass as part of the biomass.

Regarding microorganisms which make up the high content DHA containing biomass, subjects described in regard to microorganisms in the high content DHA containing oil except for the subjects specified below are directly applied as subjects replaced with microorganisms in the biomass.

In terms of the growth of microorganisms and lipid accumulation, exemplary microorganisms in the high content DHA containing biomass may include microorganisms belonging to Stramenopiles, preferably Thraustochytrid, as well as microorganisms belonging to *Alveolata*, preferably the genus *Crypthecodinium*. At least one microorganism selected from the group consisting of microorganisms of the genus *Schizochytrium*, microorganisms of the genus *Crypthecodinium*, and microorganisms of the genus *Aurantiochytrium* can be further preferably selected. Microorganisms of the genus *Aurantiochytrium* can be particularly selected. As long as these microorganisms have the capacity to produce the DHA containing oil, the microorganisms may be wild strains collected under a natural environment or may be mutants obtained by artificially or incidentally inducing mutations in the wild strains. Regarding the mutants which may form the high content DHA containing biomass, subjects described regarding the mutants in the high content DHA containing oil are replaced with mutants in the biomass and directly applied. Exemplary mutants of microorganisms in the high content DHA containing biomass may include *Aurantiochytrium limacinum* NiD2 and NiD3 strains, along with microbial strains having substantially the same microbiological properties as these microbial strains.

NiD2 and NiD3 strains, along with microbial strains having substantially the same microbiological properties as these microbial strains, can produce high content DHA containing oil containing DHA at a concentration of 40 wt. % or more of the total weight of the fatty acid with a DSC pour point of 15° C. or lower in a biomass including these microbial strains or in the cell thereof. The high content DHA containing oil produced by these microbial strains exhibits a tendency in which the content of $_{n-6}$DPA in the oil is higher than the content of that in the oil produced by the parent strains of these microbial strains, a tendency in which the content of palmitic acid is lower than the content of that in the oil produced by the parent strains of these microbial strains, or a tendency combining these.

The high content DHA containing biomass may efficiently produce DHA. The accumulative amount of DHA of the high content DHA containing biomass means the amount of DHA produced by the biomass in 1 liter of culture product and is determined as the ratio (weight ratio) of the DHA amount to the culture liquid per 1 liter of the dried biomass weight. The DHA accumulative amount of the high content DHA containing biomass, for example, can be 18 wt. % or more, 20 wt. % or more, 23 wt. % or more, 28 wt. % or more, 30 wt. % or more, 33 wt. % or more, 38 wt. % or more, 40 wt. % or more, 48 wt. % or more, 50 wt. % or more, or 53 wt. % or more of the dried biomass weight. Because the high content DHA containing biomass includes the high content DHA containing oil having such a DHA concentration, for example, the high content DHA containing oil can be efficiently obtained from the biomass by generally used extraction methods. Moreover, by taking in the high content DHA containing biomass or the high content DHA containing dried biomass as is, the high content DHA containing oil can be efficiently taken in.

(3) Manufacturing Method

The manufacturing method of the high content DHA containing oil can include: culturing organisms such as a microbial strain of the genus *Aurantiochytrium*, which may produce an oil which contains DHA at a concentration of 40 wt. % or more of the total weight of fatty acid in the oil with the endothermic peak temperature thereof determined by differential scanning calorimetry (DSC) being 15° C. or lower, that is, a high content DHA containing oil, to obtain a biomass (hereinafter, also referred to as a culture step); recovering a cultured biomass (hereinafter, also referred to as a recovery step); extracting oil from the recovered biomass (hereinafter, also referred to as the extraction step), and can further include other steps as required.

The manufacturing method of the biomass according to one aspect of the present disclosure can include the abovementioned culture step and recovery step, in addition to further including other steps as required.

The manufacturing method of the dried biomass according to one aspect of the present disclosure can include the abovementioned culture step and recovery step, and drying the biomass obtained by recovery (hereinafter, also referred to as a drying step), in addition to further including other steps as required.

In the culture step, organisms which may produce the high content DHA containing oil are cultured. The organisms used in the culture step are not limited as long as they are organisms which may produce the high content DHA containing oil. The culture conditions, culture medium, culture apparatus, and the like, which are generally applied to organisms which may produce the high content DHA containing oil, can be directly applied.

In a case where organisms which may produce the high content DHA containing oil are microorganisms, the spores or mycelia of the microbial strain or preculture liquid obtained by culturing microorganisms in advance are inoculated to a liquid or solid culture medium and be cultured. Exemplary culture media may include: carbon sources such as glucose, fructose, xylose, sucrose, maltose, starch, soluble starch, molasses, glycerol, and mannitol; nitrogen sources such as yeast extract, malt extract, meat extract, fish meat extract, corn steep liquor, peptone, polypeptone, soybean powder, defatted soybean powder, casamino acid, urea, sodium glutamate, ammonium acetate, ammonium sulfate, ammonium nitrate, ammonium chloride, and sodium nitrate; inorganic salts such as sodium chloride, potassium chloride, magnesium chloride, magnesium sulfate, calcium chloride, potassium dihydrogen phosphate, and dipotassium hydrogen phosphate; vitamins; and culture media obtained by appropriately combining necessary components. The culture medium includes sodium chloride, potassium chloride, magnesium chloride, magnesium sulfate, calcium chloride, and the like, and therefore can be applied to the culture medium of marine microorganisms. In terms of the growth potential of a wide variety of microorganisms which may produce high content DHA containing oil, for example, yeast extract glucose agar culture medium (GY medium) can be used as the culture medium. An aqueous medium used as the base material for the liquid culture medium is basically water, with distilled water or purified water capable of being used. After preparing the culture medium, the pH is adjusted to the range from 3.0 to 9.0, after which the culture medium is sterilized by an autoclave, and the like. Culturing can be carried out at a culture temperature from 10° C. to 40° C. for a period of 1 to 14 days by ventilation stirring culture, shaking culture, or stationary culture.

The spores or mycelia of the microbial strain or the preculture liquid obtained by preculturing microorganisms in advance can be inoculated to a liquid or solid culture medium and be cultured. Exemplary culture media may include: carbon sources such as glucose, fructose, xylose, sucrose, maltose, starch, soluble starch, molasses, glycerol, and mannitol; nitrogen sources including natural nitrogen sources such as yeast extract, malt extract, meat extract, fish meat extract, corn steep liquor, peptone, polypeptone, soybean powder, defatted soybean powder, and casamino acid, organic nitrogen sources such as urea, and inorganic nitrogen sources such as sodium glutamate, ammonium acetate, ammonium sulfate, ammonium nitrate, ammonium chloride, and sodium nitrate; inorganic salts such as phosphate, magnesium sulfate, iron sulfate, and copper sulfate, and trace nutrient sources such as vitamins; and culture media obtained by appropriately combining necessary components. Such a culture medium can be applied to soil derived microorganisms. An aqueous medium used as the base material for the liquid culture medium is basically water, with distilled water or purified water capable of being used.

In terms of maintenance or promotion of the growth of microorganisms, the nitrogen source in the culture medium can be from 0.01 wt. % to 10 wt. %, preferably from 0.1 wt. % to 4 wt. %. An appropriate amount of the nitrogen source can be added into the culture medium along with growth of microorganisms, with no limitation on the number of times. In the case of adding a nitrogen source, the amount of the nitrogen source to be once added can be appropriately set in terms of maintenance or promotion of the growth of microorganisms.

In terms of maintenance or promotion of the growth of microorganisms, the carbon source in the culture medium can be from 0.1 wt. % to 30 wt. %, preferably from 1 wt. % to 15 wt. %. An appropriate amount of the carbon source can be added into the culture medium along with the growth of microorganisms, with no limitation on the number of times. In the case of adding a carbon source, the amount of the carbon source to be once added can be appropriately set in terms of maintenance or promotion of the growth of microorganisms.

In a case where the following (i) to (iv) microorganisms are selected, the addition amount of sodium salt, and the addition amount of vitamins, can be selected within a specific range. In a case where the addition amount of the sodium salt and the addition amount of the vitamins are selected within a specific range, the DHA production efficiency tends to be improved due to these marine microorganisms:

(i) marine microorganisms;
(ii) as DHA highly productive microorganisms, at least one microorganism selected from the group consisting of microorganisms of the genus Thraustochytrium, microorganisms of the genus *Aurantiochytrium*, microorganisms of the genus *Schizochytrium*, microorganisms of the genus *Ulkenia*, the genus *Crypthecodinium*, and the mutants thereof;
(iii) at least one microorganism selected from the group consisting of microorganisms of the genus *Aurantiochytrium* such as *Aurantiochytrium limacinum* and *Aurantiochytrium mangrovei*, and the mutants thereof; or
(iv) at least one microorganism selected from the group consisting of *Aurantiochytrium limacinum* NiD2 and NiD3, and microbial strains having substantially the same microbiological properties as these microbial strains.

That is, in a case where these marine microorganisms, for example, DHA highly productive microorganisms, are selected, the addition amount of sodium salt to the culture medium can be selected in terms of maintenance or promotion with respect to, for example, the growth of microorganisms, synthesis of fatty acids, and synthesis of DHA, and can be from 0.001 wt. % to 10 wt. %, preferably from 0.1 wt. % to 5 wt. %, more preferably from 1.0 wt. % to 3.0 wt. %. In a case where the concentration of the sodium salt in the culture medium is presumably decreased along with the addition of the nitrogen source or the carbon source, the sodium salt concentration in the culture medium can be increased in the concentration range in advance so as not to inhibit the growth of microorganisms. An appropriate amount of sodium salt can be added to the culture medium, with no limitation on the number of times. In the case of adding sodium salt, the amount of sodium salt to be once added can be appropriately set in terms of maintenance or promotion of the growth of microorganisms.

In a case where the marine microorganisms, for example, DHA highly productive microorganisms, are selected, the addition amount of vitamins to the culture medium can be selected in terms of maintenance or promotion of the growth of microorganisms, and production suppression of odd chain fatty acids, and can be from 0.01 ppm to 50 ppm, preferably from 0.1 ppm to 10 ppm as the total amount of vitamins. Vitamins in the form of a prepared concentrated solution may be added into the culture medium. In a case where the vitamin concentration in the culture medium is presumably reduced along with the addition of the nitrogen source or the carbon source or other culture medium components, the amount of vitamins in the culture medium can be increased in the concentration range in advance so as not to inhibit the growth of microorganisms. An appropriate amount of vitamins can be added to the culture medium, with no limitation on the number of times. In the case of adding vitamins, the amount of vitamins to be once added can be appropriately set in terms of maintenance or promotion of the growth of microorganisms.

In a case where the marine microorganisms, for example, DHA highly productive microorganisms, are selected, the addition amount of metal salts in the culture medium can be selected in terms of maintenance or promotion with respect to, for example, the growth of microorganisms, synthesis of fatty acids, synthesis of DHA, and the total amount of metal salts can be from 0.0001 wt. % to 5 wt. %, preferably from 0.001 wt. % to 2 wt. %. Metal salts in the form of a prepared concentrated solution may be added to the culture medium. In a case where the metal salt concentration in the culture medium is presumably decreased along with the addition of the nitrogen source, carbon source, or other culture medium components, the amount of metal salts in the culture medium can be increased in the concentration range in advance so as not to inhibit the growth of microorganisms. An appropriate amount of metal salts can be added to the culture medium, with no limitation on the number of times. In the case of adding metal salts, the amount of metal salts to be once added can be appropriately set in terms of maintenance or promotion of the growth of microorganisms.

In a case where the marine microorganisms, for example, DHA highly productive microorganisms, are selected, the pH of the culture medium can be selected in terms of maintenance or promotion with respect to, for example, the growth of microorganisms, synthesis of fatty acids, and synthesis of DHA, and can be from 3.0 to 9.5, preferably from 3.5 to 9.5, more preferably from 4.5 to 9.0. The pH of the culture medium can be appropriately controlled by a pH adjustor such as sodium hydroxide or sulfuric acid in a case where components in the culture medium are metabolized with microorganisms so as to increase or decrease the pH.

In terms of the DHA production efficiency, the culture temperature can be, for example, 40° C. or lower, 35° C. or lower, 30° C. or lower, 28° C. or lower, or 25° C. or lower, while in terms of the growth of microorganisms, it can be 8° C. or higher, 10° C. or higher, or 15° C. or higher. The upper limit value or lower limit value of the culture temperature may be any of the following combinations, and can be, for example, from 8° C. to 40° C., from 8° C. to 28° C., from 10° C. to 40° C., from 10° C. to 25° C., or from 15° C. to 25° C. In the case of culturing in such a temperature range, the DHA concentration in the high content DHA containing oil can be increased.

No particular limitation is placed on the culture vessel used for culturing, and any device that is ordinarily used for the culturing of microbes can be used. The culture vessel may be appropriately selected according to the scale of culturing. Examples thereof may include a culture vessel which enables liquid culturing at a scale of from 1 L to 50 L. The culture vessel can include a stirring or penetration function. In the case of liquid culturing at a scale from 1 L to 50 L, a stirred-type culture vessel is preferably used as the culture vessel in order to obtain the target high content DHA containing oil at a higher concentration. The stirred-type culture vessel preferably has disc turbine-type agitator blades in at least one stage, and a stirred-type culture vessel further preferably has disc turbine type agitator blades in two stages.

While not particularly limited thereto, the culture period in the culture step differs depending on the kind and growth state of microorganisms, the accumulation efficiency of fatty acids, and the like, and can be completed when the amount of the dried biomass per 1 liter of the culture liquid reaches from 20 g to 200 g. The culture period in the culture step can be generally from 1 to 14 days, or from 3 to 10 days. The airflow rate in the ventilation culture can generally be from 0.2 vvm to 2.0 vvm, preferably from 0.5 vvm to 1.0 vvm. Moreover, the internal gauge pressure can generally be from 0.01 MPa to 0.2 MPa, preferably from 0.02 MPa to 0.1 MPa.

In the recovery step, the cultured biomass is recovered. In accordance with the kind of organisms and the kind of culture medium, the cultured biomass can be recovered from the culture medium by methods known in the art. In the recovery step, a biomass including the high content DHA containing oil is obtained. For example, in a case where a culture is carried out using a liquid culture, the recovery process can be carried out in general using a solid-liquid separation means such as centrifugation and filtration after the completion of culturing. In a case where a solid culture medium is used for culturing, the solid culture medium and the biomass may be crushed using a homogenizer and the like without separation of the biomass from the culture medium, and the crushed material obtained may be supplied to the extraction step.

In order to obtain the dried biomass, the drying step in which the biomass obtained in the recovery step if dried may be included prior to the extraction step. The drying process can be carried out by methods known in the art, such as freeze drying, air drying, or heat drying. Whether a biomass has been obtained via the drying process can be confirmed by measuring the water content. For example, the water content of a dry microbial biomass can be 10% or less. The water content can be measured based on the "Normal pressure heat drying method" described in the "Shin Shokuhin bunsekiho" (January, 1997) edited by the Japanese Society for Food Science and Technology, Food Analysis Method Editing Committee.

In the extraction step, an oil is extracted from the biomass after the recovery step to obtain an extracted oil. Generally, a standard extraction method using an organic solvent can be applied to the extraction process. In a case where the recovered biomass is dried biomass, the extraction process may involve extraction using supercritical carbon dioxide or may be an extraction process using an organic solvent under nitrogen air flow. Exemplary organic solvents that can be used in the extraction process may include: ethers such as dimethylether and diethylether; hydrocarbons having 10 or less carbons such as petroleum ether, hexane, and heptane; alcohols such as methanol and ethanol; chloroform; dichloromethane; fatty acids such as octanoic acid or alkyl esters thereof; and oils and fats such as vegetable oil. As the extraction process, extraction by alternating extraction using methanol and petroleum ether or extraction using a single layer type solvent of chloroform-methanol-water can be applied. In this case, more favorable results from the extraction process can be obtained. An extracted oil can be obtained by distilling off the organic solvent from the extract under reduced pressure. In a case where triacyl glycerol is collected or the extracted oil is extracted from microorganisms, hexane is generally used as the organic solvent. As mentioned above, crude oil refers to the extracted oil obtained immediately after the extraction process.

The high content DHA containing oil can be obtained from the extracted oil. In a case where the high content DHA containing oil is a crude oil, the high content DHA containing oil can be obtained in the extraction step. Because the extracted oil obtained in the extraction step, that is, the crude oil contains 40 wt. % or more DHA and the DSC pour point thereof is 15° C. or lower, it is relatively stable against changes in temperature, and shows an excellent stability at low temperatures and excellent handleability. For example, in a case where crude oil is applied to the extraction step or the subsequent process, the generation of clogging inside the pipe can be suppressed; and in a case where the crude oil is blended to prepare a composition, an increase in the viscosity of the composition for blending the crude oil can be suppressed to facilitate a preparation thereof.

In a case where a wet microbial biomass is used in the extraction process, the wet microbial biomass may be compressed and a solvent may be used. Exemplary solvents which can be used may include a solvent compatible with water such as methanol or ethanol, or a mixed solvent formed from a solvent compatible with water and water and/or another solvent. The remainder of the procedure is similar to that described above.

In a case where the high content DHA containing oil is crude oil, the high content DHA containing oil can have at least one, at least two, at least three, at least four, at least five, or all of the following properties. In a case where it has two or more properties, any combination of the below-mentioned (1) to (6) can be used.

(1) The acid value (AV) may be higher than 0.5 mg KOH/g, higher than 1.0 mg KOH/g, or higher than 1.5 mg KOH/g.
(2) The phospholipid concentration may be 3 wt. % or more, 5 wt. % or more, or 10 wt. % or more.
(3) The glycolipid concentration may be 3 wt. % or more, 5 wt. % or more, or 10 wt. % or more.
(4) The triglyceride concentration may be 90 wt. % or more, 92 wt. % or more, or 94 wt. % or more.

(5) The DHA concentration in triglycerides may be 50 wt. % or more, 60 wt. % or more, 70 wt. % or more, or 80 wt. % or more.

(6) The concentration of unsaponifiable substance may be more than 4.5 wt. %.

The acid value (AV) was measured in accordance with the standard methods for the analysis of fats, oils and related materials (2013 Edition) 2.3.1-2013 acid value (edited by the Japan Oil Chemists' Society).

The phospholipid concentration was measured in accordance with the standard methods for the analysis of fats, oils and related materials (2013 Edition) 2.4.11-2013 phospholipid (edited by the Japan Oil Chemists' Society).

The glycolipid concentration was determined as follows. That is, in accordance with the method described in Lipid analysis: isolation, separation, identification, and structural analysis of lipids, Christie, W. W. Oily Press: Bridgwater, England, 2003; pp 69: Chapter 4 "Analysis of simple lipid classes, A. Preliminary fractionation of lipid extracts", the fraction of glycolipids was obtained. Regarding silica gel, Sep-Pak (registered trademark) Plus Silica Cartridges (Waters Corporation) having a particle diameter from 55 μm to 105 μm, as well as a capacity of 690 mg (Sorbent weight), was used. The lipid amount obtained after removing acetone in the obtained fraction along with other solvents, if present, was measured, with the weight percentage of the obtained lipid amount to the total lipid amount serving as the glycolipid concentration.

Based on the specific method described in the quantitative determination of unsaponifiable substance of the standard methods for the analysis of fats, oils and related materials by the Japan Oil Chemists' Society, the concentration of unsaponifiable substance was obtained by saponifying oil and fat, removing the mixed fatty acid amount from the extracted material in a solvent used for quantitative determination, and representing it as the percentage in a sample. Note that, for example, the amount of unsaponifiable substance such as tocopherol added after refining is subtracted. The outline of the abovementioned specific method is as follows (refer to Oil Chemistry, 13, 489(1996)).

A sample of approximately 5 g is taken in a flask, after which 50 ml of 1N-ethanol-potassium is added thereto, gently boiled for 1 hour, and saponified. Once saponification is complete, heating is stopped, and the flask for saponification is washed with 100 ml of warm water, while a liquid obtained after saponification is transferred into a separatory funnel, after which 50 ml of water is added thereto, and cooled until it reaches room temperature. Next, 100 ml of ethyl ether is added to the separatory funnel while the flask for saponification is washed. The separatory funnel is hermetically sealed, shaken hard for 1 minute, mixed, and left to stand until it is clearly divided into two layers. The divided lower layer is transferred into a second separatory funnel, 50 ml of ethyl ether is added thereto, shaken and mixed as in the first separatory funnel, then left to stand. In a case where it is divided into two layers, the lower layer is transferred to a third separatory funnel and extraction is similarly repeated using 50 ml of ethyl ether.

Each separatory funnel of the ethyl ether layer in the second and third separatory funnels is washed with a small amount of ethyl ether and transferred to the first separatory funnel, after which 30 ml of water is added thereto, shaken, and mixed, subsequently left to stand, and divided into two layers to remove the lower layer. Furthermore, each time, 30 ml of water is added, shaken, and mixed, left to stand, and separated, after which this is repeated, then the separated water is washed until it is no longer colored with a phenolphthalein indicator. The washed ethyl ether extracted liquid is subjected to a dehydration process with sodium sulfate (anhydrous) as required, filtrated with dried filter paper, then transferred to a distillation flask. Several containers, filter paper, and the like used for the extraction are all washed with a small amount of ethyl ether, and a washing liquid is added to the distillation flask. Ethyl ether in the distillation flask is distilled and removed, then cooled in a case where the liquid amount thereof reaches approximately 50 ml. Subsequently, the flask is washed with a small amount of ethyl ether, while the concentrated ethyl ether extract is transferred to a 100 ml round bottom flask with the weight thereof precisely measured in advance.

Most of the ethyl ether in the round bottom flask is distilled and removed, 3 ml of the acetone is subsequently added, the majority thereof is distilled and removed as before, for example, the extract is heated under slightly reduced pressure of approximately 200 mmHg at 70 to 80° C. for 30 minutes, and the round bottom flask is transferred to a vacuum desiccator, left to stand for 30 minutes, and cooled. The weight of the round bottom flask is precisely measured to determine the weight of the extract. 2 ml of ethyl ether and 10 ml of neutral ethanol are added to the round bottom flask and sufficiently shaken and mixed to dissolve the extract, then the amount of mixed fatty acids is determined in an N/10-ethanol-potassium standard solution using the phenolphthalein indicator. Here, the end point is reached when the slightly red color of the titration indicator is maintained for 30 seconds.

$$\text{Unsaponifiable substance concentration (\%)}=A-(B\times F\times 0.0282)/C\times 100$$

$$\text{mixed fatty acid (as oleic acid, g)}=B\times F\times 0.0282$$

wherein

A=weight (g) of the extract

B=usage amount (ml) of the N/10-ethanol-potassium standard solution

C=amount (g) of the sample collected

F=potency of the N/10-ethanol-potassium standard solution

The triglyceride concentration was measured in accordance with AOCS Recommended Practice Cd 11c-93 (1997), SAMPLING AND ANALYSIS OF COMMERCIAL FATS AND OILS, (American Oil Chemists' Society).

In a case where the high content DHA containing oil is a refined oil, the manufacturing method of the high content DHA containing oil can include, after the extraction step, the refining process in which the obtained extracted oil, that is, crude oil is subjected to the refining step including a degumming step, deacidification step, decoloring step, and deodorizing step. The high content DHA containing oil as the refined oil can be obtained in the refining process. In a case where the extracted oil derived from a microbial biomass is subjected to the refining process, a triacyl glycerol concentrate having a higher triacyl glycerol concentration than the crude oil is mainly obtained.

In the refining step, degumming, deacidification, decoloring, and deodorizing are performed on the crude oil with methods used for the purification of vegetable oil, fish oil, and the like using methods known to those skilled in the art. The degumming process is carried out, for example, by the washing process, and the like. The deacidification process is carried out, for example, by the distillation process, and the like. The decoloring process is carried out, for example, by the decoloring process using activated white clay, activated carbon, silica gel, and the like. The deodorizing process is carried out, for example, by steam distillation, and the like. Because the refined oil obtained in the refining step contains 40 wt. % or more DHA and the DSC pour point thereof is 15° C. or lower, it is relatively stable against changes in temperature and shows excellent stability at low temperatures. Therefore, as with crude oil, in the refining step or the subsequent process, the generation of clogging inside a pipe can be suppressed, resulting in excellent handleability.

The refined oil obtained after the refining step may have a triglyceride concentration of 95 wt. % or more and satisfy at least one condition selected from the group consisting of the following (P1) to (P4), or may satisfy at least one condition selected from the group consisting of the following (P1) to (P4) and have a DHA concentration in triglyceride of 50 wt. % or more, 60 wt. % or more, 70 wt. % or more, or 80 wt. % or more.
(P1) the acid value (AV) is 0.5 mg KOH/g or lower,
(P2) the phospholipid concentration is less than 3 wt. %,
(P3) the glycolipid concentration is less than 3 wt. %, and
(P4) the concentration of unsaponifiable substance is 4.5 wt. % or less.

The manufacturing method of the high content DHA containing oil can include a processing step in which the crude oil or the refined oil is subjected to processing such as hydrolysis, alkyl esterification and the like after the extraction step, or as the case may be, after the extraction step and the refining step. In the processing step, a composition containing free fatty acids, a composition containing fatty acid lower alkyl esters, and the like can be obtained. In particular, in a case where the manufacturing method of the high content DHA containing oil includes the refining step and processing step in this order after the extraction step, free fatty acids, fatty acid lower alkyl esters, and the like, derived from a triacyl glycerol concentrate obtained in the refining step, can be obtained. The alkyl esterification process and hydrolysis process in the processing step can be carried out under conditions known to those skilled in the art.

Lower alcohols are used in the alkyl esterification process. Exemplary lower alcohols may include alcohols having from 1 to 3 carbons such as methanol, ethanol, and propanol. For example, the fatty acid methyl esters are obtained by processing the extracted oil at room temperature for 1 to 24 hours using from 5% to 10% anhydrous methanol/hydrochloric acid, from 10% to 50% BF3/methanol, and the like. The ethyl esters of the fatty acids are obtained by processing the extracted oil for 15 to 60 minutes at 25° C. to 100° C. using from 1% to 20% sulfuric acid ethanol, and the like. The methyl esters or ethyl esters may be extracted from the reaction liquid using an organic solvent such as hexane, diethylether, or ethyl acetate. The extract liquid is dried using anhydrous sodium sulfate or the like, after which the organic solvent is removed by distillation to obtain a composition mainly composed of fatty acid alkyl esters.

The hydrolysis process may be carried out under conditions known to those skilled in the art, for example, such that extracted oil is subjected to an alkaline decomposition process with 5% sodium hydroxide at room temperature for 2 to 3 hours, after which a composition containing free fatty acids can be obtained from the obtained decomposition liquid using a method regularly used for the extraction or refining of fatty acids.

In order to obtain free fatty acids, both the alkyl esterification process and the hydrolysis process may be carried out. In a case where the alkyl esterification process and the hydrolysis process are continuously carried out, free fatty acids of a higher purity can be obtained. In order to obtain free fatty acids from fatty acid alkyl esters, for example, after hydrolysis using an alkaline catalyst, the extraction process may be performed using an organic solvent such as ether and ethyl acetate.

The manufacturing method of the high content DHA containing oil can include a concentration process after the refining step or processing step, in order to reduce the concentration of fatty acids in which fatty acids other than DHA is constituent fatty acids and to increase the DHA concentration. For concentration process, distillation, rectification, column chromatography, low temperature crystallization method, urea clathrate method, liquid-liquid countercurrent distribution chromatography, and the like may be used alone or in combination of two or more. A combination of distillation or rectification, along with column chromatography or liquid-liquid countercurrent distribution chromatography is preferably used. Reverse phase distribution type column chromatography is preferable for column chromatography. When the step of concentrating or isolating DHA is performed, the content of DHA, which may be finally contained in the high content DHA containing oil, in the fatty acids can be increased and the content of fatty acids other than DHA in the fatty acids can be decreased.

For example, for the case in which rectification is used, the rectification step is preferably carried out by distillation under a reduced pressure at the upper part of the distillation column of less than or equal to 10 mmHg (1333 Pa), and temperature of the column bottom in the range from 165° C. to 210° C., preferably from 170° C. to 195° C., from the perspective of suppressing the denaturation of fatty acids by heating and increasing the efficiency of rectification. The pressure of the upper part of the distillation column is preferably as low as possible, preferably 0.1 mmHg (13.33 Pa) or lower. No particular limitation is placed on the temperature at the upper part of the column, and for example, this temperature may be set to 160° C. or lower. In the rectification step, a composition having an even higher content of DHA may be obtained.

The reverse phase column chromatography may be a type of reverse phase column chromatography that is known in the art, and high-performance liquid chromatography (HPLC) using a substrate modified by octadecylsilyl groups (ODS) as a stationary phase is particularly preferable.

By carrying out such a concentration process, a DHA concentrated oil having a DHA concentration, for example, from 90 wt. % to 98 wt. %, from 95 wt. % to 98 wt. %, from 96 wt. % to 98 wt. %, or from 97 wt. % to 98 wt. % of the total weight of fatty acid in the oil, can be obtained.

(4) Use

The high content DHA containing oil and high content DHA containing biomass DHA can be applied for uses in which various functions are required to efficiently obtain. Exemplary products containing the high content DHA containing oil and high content DHA containing biomass may include food products, supplements, medicaments, cosmetics, animal feed, and the like. The high content DHA containing oil and high content DHA containing biomass can be used in the manufacturing method of these products. In particular, exemplary uses as the high content DHA containing oil and high content DHA containing biomass include food products, supplements, medicaments, cosmetics, animal feed, and the like which include DHA as an effective component, and are expected to be effective in terms of the prevention of lifestyle related diseases such as arteriosclerosis, cerebral infarction, myocardial infarction, thrombosis, and hyperlipemia, improvement of metabolic syndrome, antiallergies, antiinflammation, and anticancer, improved brain function, and improved stress. Exemplary medicaments include external medicines for skin and oral preparations.

The use form of the high content DHA containing oil, high content DHA containing biomass, and high content DHA containing dried biomass is not particularly limited and can be used as liquid components or solid components. For example, in a case where the high content DHA containing oil, high content DHA containing biomass, or high content DHA containing dried biomass is applied to products such as food products, supplements, medicaments, cosmetics, and animal feed, the high content DHA containing oil, high content DHA containing biomass, or high content DHA containing dried biomass itself may be combined with other components for commercialization or can be subjected to additional processes before or after being combined with other components for commercialization. Exemplary additional processes may include powderization, pelletization, capsulation, tableting, and the like.

In a case where the high content DHA containing oil, high content DHA containing biomass, and high content DHA containing dried biomass are used as medicaments, medicaments include the high content DHA containing oil, high content DHA containing biomass, and high content DHA containing dried biomass, pharmaceutically acceptable carriers and, optionally, other components. The dosage form may be any form which is convenient for oral administration or parenteral administration. Exemplary dosage forms include injections, transfusions, powders, granules, tablets, capsules, enteric coated tablets, troches, peroral liquid preparations, suspensions, emulsions, syrups, liquids for external use, fomentations, nasal preparations, ear drops, eye drops, inhalants, ointments, lotions, and suppositories. These may be used individually or in combination depending on the symptoms.

By standard methods, these various types of preparations, depending on the purpose, may be formulated by adding, to the principle agent, previously known adjutants commonly used in the field of drug preparation technology, as exemplified by excipients, binders, preservatives, stabilizers, disintegrants, lubricants, flavoring agents, and the like. Furthermore, in the case of oral administration to adults, typically, the dosage for administration can be appropriately adjusted within a range from 0.01 mg to 10 g, preferably from 0.1 mg to 2 g, and more preferably from 1 mg to 200 mg, per day as the total amount of DHA as a structured lipid. In the case of parenteral administration, the dosage for administration can be appropriately adjusted within a range from 0.001 mg to 1 g, preferably from 0.01 mg to 200 mg, and more preferably from 0.1 mg to 100 mg, per day as the total amount of DHA as a structured lipid. These dosages differ depending on the purpose of the administration, along with the conditions of the person subjected to administration, for example, sex, age, weight, and the like.

In the present specification, the features described in the embodiments related to each aspect of the disclosure may be combined as desired to form new embodiments, and it is to be understood that such new embodiments may be included in each of the aspects of the present disclosure.

EXAMPLES

The present disclosure is described below in detail using examples. However, the present disclosure is not limited in any manner by these examples. Unless otherwise specified, "part" or "%" is indicated on a mass basis.

Unless otherwise specified, in the following examples, "cell(s)" or "microbial body(ies)" mean an aggregation of cells or microbial bodies, corresponding to the biomass in the present specification.

Example 1

Isolation and Identification of the NBL-8 Strain

Mud was collected from the brackish water region of Ishigaki Island. The obtained mud was appropriately diluted with artificial seawater, applied to an agar culture medium for Thraustochytrid including 1 mg/ml of ampicillin, and cultured at 26° C. On the third day of culturing, multiple microbial strains for forming colonies were collected in the culture medium, one of which was named the NBL-8 strain.

The NBL-8 strain has a life history of vegetable cells and zoospores in a liquid culture medium for Thraustochytrid, wherein the vegetable cells of the NBL-8 strain do not exhibit motility and are proliferated mainly by continuous binary fission. The NBL-8 strain forms zoosporangia and forms multiple zoospores in the zoosporangia. Subsequently, the zoospores are released outside the zoosporangia to serve as zoospores. The zoospores are grounded after a certain period of swimming to serve as vegetable cells. Such a life history is characteristic of the kingdom Chromista, the class Labyrinthulea, the family Thraustochytriaceae, the genus *Aurantiochytrium*, and the species limacinum (refer to Honda et. al., Mycological Research. 102(4):439-448 (1998); Yokoyama and Honda, Mycoscience. 48(4):199-211 (2007)). From the analytical results of the 16S rRNA gene sequence as well, the NBL-8 strain is recognized as *Aurantiochytrium limacinum*.

Note that the name of *Aurantiochytrium limacinum* during the report that it is separated is *Schizochytrium limacinum*. The classification of the family Thraustochytriaceae was reviewed by Honda et. al. in 2007, and renamed *Aurantiochytrium* (refer to the abovementioned document).

Each composition of artificial seawater, an agar culture medium for Thraustochytrid, and a liquid culture medium for Thraustochytrid, which was used to isolate the NBL-8 strain, is indicated in Tables 1 to 3. A vitamin solution obtained by dissolving each composition, sterilizing it with a filter, and storing it at −20° C. was used. A metal salt solution obtained by dissolving each composition, sterilizing it, and storing it at 4° C. was used. These solutions mentioned above were also used in the following examples.

Each composition of the vitamin solution (*) and the metal salt solution (**) in Tables 2 and 3 is indicated in Tables 4 and 5.

TABLE 1

| Artificial seawater (1 liter) | |
|---|---|
| NaCl | 15 g |
| KCl | 0.35 g |
| $MgCl_2 \cdot 6H_2O$ | 5.4 g |
| $MgSO_4 \cdot 7H_2O$ | 2.7 g |
| $CaCl_2 \cdot 2H_2O$ | 0.5 g |
| Deionized water | Residual |

TABLE 2

| Agar culture medium for Thraustochytrid (1 liter) | |
|---|---|
| Glucose | 30 g |
| Yeast extract | 20 g |

TABLE 2-continued

Agar culture medium for
Thraustochytrid (1 liter)

| | |
|---|---|
| NaCl | 15 g |
| KCl | 0.35 g |
| MgCl$_2$•6H$_2$O | 5.4 g |
| MgSO$_4$•7H$_2$O | 2.7 g |
| CaCl$_2$•2H$_2$O | 0.5 g |
| Vitamin solution * | 1.0 mL |
| Metal salt solution ** | 2.0 mL |
| Agar powder | 15 g |
| Deionized water | Residual |

TABLE 3

Liquid culture medium
for Thraustochytrid (1 liter)

| | |
|---|---|
| Glucose | 30 g |
| Yeast extract | 20 g |
| NaCl | 15 g |
| KCl | 0.35 g |
| MgCl$_2$•6H$_2$O | 5.4 g |
| MgSO$_4$•7H$_2$O | 2.7 g |
| CaCl$_2$•2H$_2$O | 0.5 g |
| Vitamin solution * | 1.0 mL |
| Metal salt solution ** | 2.0 mL |
| Deionized water | Residual |

TABLE 4

Vitamin solution (1 liter)

| | |
|---|---|
| Thiamine | 200 mg |
| Riboflavin | 1.0 mg |
| Cyanocobalamin | 1.0 mg |
| Deionized water | Residual |

TABLE 5

Metal salt solution (1 liter)

| | |
|---|---|
| Na$_2$EDTA | 30 g |
| FeCl$_3$•6H$_2$O | 1.43 g |
| H$_3$BO$_3$ | 34.2 g |
| MnCl$_2$•4H$_2$O | 4.3 g |
| ZnSO$_4$•7H$_2$O | 1.335 g |
| CoCl$_2$•6H$_2$O | 0.13 g |
| NiSO$_4$•H$_2$O | 0.26 g |
| CuSO$_4$•H$_2$O | 0.01 g |
| Na$_2$MoO$_4$•2H$_2$O | 0.025 g |
| Deionized water | Residual |

Example 2

Freeze Storage of the NBL-8 Strain

Colonies of the NBL-8 strain formed on an agar culture medium plate for Thraustochytrid were collected with a sterilized inoculating loop and inoculated into 500 ml of a sterilized ribbed shaking flask containing 100 ml of a liquid culture medium for Thraustochytrid. This flask was shaken at 28° C. at 120 rpm for 2 to 5 days. TXY-25R-2F available from Takasaki Kagaku Kikai Co., Ltd., (now, Preci Co., Ltd.) was used for culturing.

Subsequently, 20 ml of the obtained cultured cell suspension obtained by culturing in a shaking flask for 2 to 5 days was collected in 50 ml of a sterilized test tube and centrifuged to recover cells. The recovered cells were washed twice with artificial seawater. Subsequently, the recovered cells, that is, the NBL-8 strain, were suspended in 20 ml of artificial seawater including a final concentration of 10 wt. % glycerol and 5 wt. % trehalose again. This served as a frozen cultured cell liquid of the NBL-8 strain and was frozen and stored at −80° C. until use in each experiment.

Example 3

Acquisition of the Mutant 0.1 ml of the frozen cultured cell liquid of the NBL-8 strain was inoculated into 500 ml of a sterilized ribbed shaking flask containing 100 ml of a liquid culture medium for Thraustochytrid. This flask was shaken at 28° C. at 120 rpm for 2 days. 20 ml of the obtained cultured cell suspension after culture was transferred into a 50 ml sterilized test tube. Subsequently, cells in the cultured cell suspension were recovered by centrifugation. The recovered cells were twice washed with sterile artificial seawater.

Next, in order to prompt the release of zoospores, the recovered cells were shaken in artificial seawater. Specifically, 20 ml of the recovered cells and artificial seawater were placed in a sterilized test tube and the obtained cell suspension was shaken at 200 rpm for 30 minutes. Next, as a mutation inducing reagent, N-methyl-N'-nitro-nitrosoguanidine (NTG) was appropriately added to the cell suspension, so as to give a death ratio of 99% or higher, and shaken at 200 rpm for 1 to 30 minutes to induce mutation. Cells subjected to the mutation inducing process were appropriately diluted with artificial seawater, applied on an agar culture medium plate for Thraustochytrid, and cultured at 28° C. for 2 to 5 days.

Colonies formed on the agar culture medium plate were selected with a sterilized inoculating loop, after which each of the colonies was streaked onto a new agar culture medium plate for Thraustochytrid again and cultured. This operation was repeated twice to isolate the mutant. The cultured cell suspension was obtained from the isolated colonies as in Example 2. From 1 ml to 10 ml of this cultured cell suspension was collected, centrifuged and frozen at −80° C. as in Example 2, then supplied to a freeze drying machine (VA-140S available from TAITEC Corporation) to obtain the freeze dried microbial body of a mutant.

The total lipid, that is, the microbial oil, was obtained from the obtained freeze dried microbial body and converted to a fatty acid methyl ester.

Specifically, in accordance with the method (J. Biological and Chemistry. 226:497-509(1957)) by Folch et. al., the total lipid was extracted from the freeze dried microbial biomass using chloroform:methanol (2:1, v/v). The obtained total lipid was subjected to methyl esterification to obtain a fatty acid methyl ester (FAME). FAME analysis was carried out on the obtained FAME using gas chromatography. The conditions of gas chromatograph were set as follows.

Column: DB-WAX of 0.530 mm×30 m, film thickness of 1.00 μm (Agilent Technologies)

Carrier gas conditions: helium of 1.0 ml/minute, separation ratio of 100:1

Column temperature conditions: at 140° C. for 5 minutes; the temperature raised by 4° C./minute to 240° C.; and at 240° C. for 10 minutes Detection: FID Detector temperature: 260° C.

Inlet temperature: 250° C.

Injected quantity: 1 μL

As a result of the FAME analysis, 6 of 200 strains of the mutant with the increased DHA concentration in the fatty acid were obtained. Among the parent strains having an indefinite circular colony shape and a undulate edge shape, those colonies having a more circular colony shape, an edge closer to the entire edge, and a smaller size were collected, with all of these colonies exhibiting common properties. Two among these were the NiD2 strain and the NiD3 strain. In accordance with the method described in Example 2, the obtained DHA concentration increasing strains were cultured, frozen, and stored.

Example 4

Production of the DHA Microbial Oil 0.1 ml of the NBL-8 or NiD2 frozen cell liquid was inoculated into 500 ml of a sterilized ribbed shaking flask containing 100 ml of a liquid culture medium for Thraustochytrid. This flask was shaken at 28° C. at 120 rpm for 2 to 3 days. The obtained cell suspension served as the culture liquid to be inoculated in a jar fermenter.

0.5 L of the culture medium including 60 g glucose, 10 g yeast extract, 15 g NaCl, 0.35 g KCl, 5.4 g $MgCl_2 \cdot 6H_2O$, 2.7 g $MgSO_4 \cdot 7H_2O$, 0.5 g $CaCl_2 \cdot 2H_2O$, 1.0 mL of a vitamin solution, and 2.0 mL of a metal salt solution was placed in a fermentation tank having a capacity of 1 L, and 1% amount (v/v) of the culture liquid was inoculated therein.

Under the conditions of a culture temperature of 20° C., 26° C. or 32° C., a stirring speed of 600 rpm, an air flow rate of 1 vvm, an internal gauge pressure of 0 MPa, and a pH of 7.0±0.5, culturing was carried out for 1 to 3 days. Subsequently, for 6 days, a feed liquid indicated in Table 6 was repeatedly added so as to give a glucose concentration of 6 wt. % or less in the culture medium and continue culturing. In a case where a large amount of foaming occurred during culturing, an antifoam was appropriately added. As the antifoam, a soybean oil, KM-72F, and the like can be used.

TABLE 6

| Feed liquid (1 liter) | |
| --- | --- |
| Glucose | 500 g |
| NaCl | 15 g |
| Ammonium Sulfate | 9.8 g |
| Monosodium Glutamate | 27.8 g |
| Deionized water | Residual |

Subsequently, 2 ml of the cultured cell suspension was collected in a 2 ml weighed centrifuge tube and centrifuged using a trace high speed cooling centrifuge to recover a microbial body. This washing process was carried out several times and the microbial body was heated and dried at 105° C. Subsequently, it was weighed to calculate the dry cell weight (DCW). DCW was measured three times to obtain the average value thereof. MX-300 available from Tomy Seiko Co., Ltd. was used as the trace high speed cooling centrifuge.

Moreover, 10 ml of the cultured cell suspension was collected in a 15 ml centrifuge tube, the freeze dried microbial body was obtained as in Example 2, the total lipid was obtained from the freeze dried microbial body as in Example 3, the total lipid was subjected to methyl esterification to obtain a fatty acid methyl ester, FAME analysis was carried out by gas chromatography, and further, the fatty acid amount and DHA accumulative amount per dry microbial body were calculated.

0.1 ml of the frozen cell liquid of the NBL-8 or NiD2 was inoculated into a 500 ml sterilized ribbed shaking flask containing 100 ml of a liquid culture medium for Thraustochytrid. This flask was shaken at 22° C. and 20° C. at 120 rpm for 3 to 4 days.

Subsequently, it was weighed to calculate the dry cell weight (DCW). DCW was measured three times to obtain the average value thereof.

The fatty acid composition (wt. %) of the fatty acid obtained from the NBL-8 or NiD2 strain, the amount of dried biomass per 1 liter of the culture liquid, the total fatty acid amount per 1 liter of the culture liquid, the DHA amount per 1 liter of the culture liquid, and the DHA production efficiency are indicated in Table 7.

Hereinafter, also in the table, the amount of dried biomass per 1 liter of the culture liquid is denoted by "DCW (g/L)", the total fatty acid amount per 1 liter of the culture liquid is denoted by "TFA (g/L)", the DHA amount per 1 liter of the culture liquid is denoted by "DHA (g/L)", and the DHA production efficiency is denoted by "DHA (vsDCW)." Moreover, "others" in the table indicates the concentration of other fatty acids.

Regarding the concentration of various fatty acids in the fatty acids produced by the NiD2 strain cultured at 20° C., DHA was 50 wt. % or more, while C16:0 was less than 30 wt. %. In contrast, regarding the concentration of various fatty acids in the total fatty acid produced by the NBL-8 strain cultured at 20° C., DHA was less than 40 wt. %, while C16:0 was 30 wt. % or more.

Similarly, the DHA concentration in the fatty acids produced by the NiD2 strain cultured at 26° C. or 32° C. was higher than the DHA concentration in the fatty acids produced by the NBL-8 strain cultured at the same temperature.

The DHA production efficiency of all of the NiD2 strains was 20 wt. % or more at the culture temperature, with each higher than the cultured NBL-8 strain at the same culture temperature.

Moreover, under all conditions, in the microbial oil of the NiD2 strain, the concentration of C12:0 was 0.1 wt. % or less.

The acid value (AV) in the microbial oil obtained from the NBL-8 strain and NiD2 strain, along with each concentration of the phospholipids, glycolipids, and unsaponifiable matter were determined in accordance with the method described in the present specification, wherein the acid value (AV) was higher than 0.5 mg KOH/g, the phospholipid concentration was 3 wt. % or more, the glycolipid concentration was 3 wt. % or more, and the concentration of unsaponifiable matter was more than 4.5 wt. %.

Moreover, in the microbial oil of other microbial strains obtained as in the microbial oil of the NiD2 strain, the triglyceride concentration was 90 wt. % or more, the DHA concentration in triglyceride was 50 wt. % or more, the phospholipid concentration was 5 wt. % or more, and the glycolipid concentration was 3 wt. % or more.

TABLE 7

| | Culture strain | | | | | |
| --- | --- | --- | --- | --- | --- | --- |
| | NBL-8 | | | NiD2 | | |
| | Culture temperature (° C.) | | | | | |
| | 20 | 26 | 32 | 20 | 26 | 32 |
| C14:0 | 3.4 | 4.3 | 3.9 | 3.6 | 3.0 | 2.2 |
| C16:0 | 37.2 | 43.4 | 44.4 | 25.7 | 29.9 | 29.5 |
| C18:0 | 0.9 | 1.1 | 1.4 | 0.7 | 0.7 | 0.8 |
| C22:5n-6 | 8.8 | 8.8 | 9.8 | 10.0 | 9.4 | 10.2 |
| C22:6n-3 | 45.4 | 38.3 | 35.2 | 51.2 | 47.1 | 44.4 |

TABLE 7-continued

| | Culture strain | | | | | |
|---|---|---|---|---|---|---|
| | NBL-8 | | | NiD2 | | |
| | Culture temperature (° C.) | | | | | |
| | 20 | 26 | 32 | 20 | 26 | 32 |
| others | 4.3 | 4.0 | 5.3 | 8.9 | 10.0 | 12.9 |
| DCW(g/L) | 88.8 | 84.2 | 84.2 | 70.6 | 65.9 | 51.7 |
| TFA(g/L) | 47.8 | 46.9 | 46.7 | 35.2 | 34.2 | 25.8 |
| DHA(g/L) | 21.7 | 18.0 | 16.5 | 18.0 | 16.1 | 11.4 |
| DHA(vs DCW) | 24.44% | 21.38% | 19.60% | 25.50% | 24.43% | 22.05% |

Example 5

Production of High Content DHA by Low Temperature Culture 0.1 ml of the frozen cell liquid of the NiD2 strain was inoculated into a 500 ml sterilized ribbed shaking flask containing 100 ml of a liquid culture medium for Thraustochytrid. This flask was shaken at 10° C. at 120 rpm for 1 month. Subsequently, DCW measurement and FAME analysis were carried out by the same method as in Example 4, and further, the fatty acid amount and DHA accumulative amount per dry microbial body were calculated.

The composition (wt. %) of the fatty acids produced by the NiD2 strain cultured at 10° C., as well as the DHA concentration (wt. %) thereof, are indicated in Table 8.

The DHA concentration of the fatty acids produced at 10° C. was 70.5 wt. %. Moreover, the concentration of C12:0 was 0.1 wt. % or less.

TABLE 8

| C14:0 | 1.0 |
|---|---|
| C16:0 | 16.1 |
| C18:0 | 0.6 |
| C22:5n − 6 | 8.9 |
| C22:6n − 3 | 70.5 |
| others | 2.9 |

Example 6

Properties of the Microbial Oil

Microbial oils were each extracted as follows from part of the NBL-8 or NiD2 strain obtained in Example 4, as well as the NiD3 strain cultured under the same conditions as in Example 2.

A cultured microbial body was heated and pasteurized, collected, centrifuged, washed, and heated and dried to obtain dry cells. 5-fold the amount (w/v) of hexane was added to the dry cells to crush cells using a homogenizer. A suspension including this cell crushed matter was centrifuged to recover a hexane layer including a microbial oil. This operation was carried out three times. Subsequently, hexane was distilled off with an evaporator to obtain a microbial oil.

The obtained microbial oil was transferred into a sample bottle, the air in the upper part of the sample bottle was substituted with nitrogen, and the bottle was sealed. This microbial oil was stored at −80° C. until it was used for analysis.

With the extracted microbial oil serving as the target, the DSC pour point was measured as follows in accordance with the method described in the document (Govindapillai et. al., (2009), Lubirication Science. 21:13-26).

10 mg of a measurement sample was weighed in a sample pan using a differential scanning calorimetry apparatus DSC 3500 Sirius (available from NETZSCH), heated at 50° C. for 5 minutes, and cooled at a cooling speed of 3° C./minute from 50° C. to −60° C.; subsequently, the temperature was raised at a temperature raising rate of 10° C./minute from −60° C. to 50° C. for measurement to obtain the DSC curve. The temperature at the maximum value of the endothermic peak in the obtained DSC curve was the DSC pour point (° C.).

The pour point was measured using the method described in Testing Methods for Pour Point and Cloud Point of Crude Oil and Petroleum Products by the Japanese Industrial Standard (JIS K 2269-1987).

1000 mg of the microbial oil as the precipitate amount was collected in a weighed micro test tube having a capacity of 2 ml available from Eppendorf Japan and left to stand at 25° C. for 1 hour, after which the precipitate was recovered using a trace high speed cooling centrifuge and the precipitate weight was measured using a precision balance, calculated as the wt. % in 1000 mg of the microbial oil. MX-300, available from Tomy Seiko Co., Ltd. was used as the trace high speed cooling centrifuge.

The fatty acid composition (wt. %), DSC pour point, pour point, and precipitate amount of the microbial oil used in the experiment are indicated in Table 9. As indicated in Table 9, irrespective of the culture temperature, the microbial oil obtained from the NiD2 and NiD3 strains had a low DSC pour point of 0° C. or lower, further had a low pour point of 0° C. or lower, and had a smaller precipitate amount than the NBL-8 strain. Moreover, it was found that the NiD2 strain and NiD3 strain have significantly lower DSC pour points than the NBL-8 strain serving as the parent strain and exhibit better handleability at low temperatures than the NBL-8 strain. Even in a case where the temperature of the microbial oil thus obtained from the NiD2 strain and NiD3 strain is reduced from room temperature, fluidity tends not to change, resulting in excellent clearness as well as excellent handleability at low temperatures.

It was found that because external measurement environment factors tend to have no influence during measurement using the DSC pour point, the measured values are advantageously stable, and further, the use of the DSC pour point allows the properties of microbial oils based on the fatty acid composition to be grasped as the overall microbial oil more accurately than the pour point according to JIS K 2269-1987.

TABLE 9

| | NBL-8 | | NiD2 | | | NiD3 |
|---|---|---|---|---|---|---|
| | Culture temperature | | | | | |
| | 20 | 26 | 20 | 26 | 32 | 28 |
| C14:0 | 3.4 | 4.1 | 3.8 | 3.0 | 2.2 | 3.0 |
| C16:0 | 35.0 | 39.3 | 26.4 | 29.1 | 28.6 | 31.1 |
| C18:0 | 0.9 | 1.1 | 0.7 | 1.0 | 1.2 | 1.2 |
| C22:5n-6 | 9.1 | 9.5 | 10.4 | 10.1 | 10.9 | 12.0 |
| C22:6n-3 | 47.5 | 41.9 | 53.1 | 50.3 | 47.9 | 48.0 |
| others | 4.1 | 4.3 | 5.5 | 6.4 | 9.1 | 4.6 |
| DSC flow point (° C.) | 16.6 | 19.1 | −9.1 | −12.1 | −10.4 | −5.8 |
| Flow point (° C.) | 2.5 | 5.0 | −10.0 | −7.5 | −7.5 | −5.0 |
| Precipitate amount (%) | 14 | 54 | 1 | 3 | 7 | 5 |

Next, when the properties of each of the microbial oils obtained by culturing the NiD2 strain or NBL-8 strain at 20° C. were subjected to sensory evaluation based on smoothness, the microbial oil derived from the NiD2 strain was smooth, giving it a preferable feel as a food product. In contrast, in the microbial oil derived from the NBL-8 strain, it felt rough, giving it unfavorable feel as a food product. It was found that the roughness of the microbial oil of the NBL-8 strain is presumably due to crystals generated in the microbial oil, while in the microbial oil derived from the NiD2 strain, the crystallization speed is suitably adjusted, and consequently, a favorable feel as a food product is obtained.

The microbial oil derived from the obtained NiD2 strain and NiD3 strain can be subjected to a refining process including the degumming step, deacidification step, decoloring step, and deodorizing step, to obtain a refined oil.

Moreover, the microbial oil derived from the obtained NiD2 strain and NiD3 strain, or the refined oil thereof can be subjected to the alkyl esterification process by standard methods using a lower alcohol, to obtain a composition containing DHA alkyl ester. The microbial oil derived from the obtained NiD2 strain and NiD3 strain, or the refined oil thereof, can be subjected to an alkaline decomposition process, for example, with 5% sodium hydroxide at room temperature for 2 to 3 hours, after which a composition containing a free DHA can be obtained from the obtained decomposition liquid using a method regularly employed for the extraction or refining of fatty acids.

Furthermore, the thus obtained DHA alkyl ester containing composition or free DHA containing composition can undergo a concentration process such as distillation, rectification, column chromatography, the low temperature crystallization method, the urea clathrate method, or liquid-liquid countercurrent distribution chromatography to obtain a concentrated DHA containing composition having a higher DHA content.

Therefore, the present disclosure enables the provision of a DHA containing oil, microbial oil, and biomass, which contain high content DHA, have excellent stability at low temperatures, and exhibit favorable handleability. Such a DHA containing oil, microbial oil, and biomass can be preferably applied for uses such as in medicaments and supplements.

Disclosure of JP 2015-234985 filed on Dec. 1, 2015 is incorporated herein in its entirety by reference.

All documents, patent applications, and technical specifications stated in the present specification are incorporated by citation in the present specification to the same degree as stated to be incorporated by reference specifically and individually.

What is claimed is:

1. A docosahexaenoic acid containing oil, the oil comprising:
    docosahexaenoic acid at a concentration of 43 wt. % to 98 wt. % of the total weight of fatty acid in the oil, wherein the oil has an endothermic peak temperature, as determined by differential scanning calorimetry (DSC), of 15° C. or lower.

2. The docosahexaenoic acid containing oil according to claim 1, wherein the endothermic peak temperature, as determined by differential scanning calorimetry (DSC), is 10° C. or lower.

3. The docosahexaenoic acid containing oil according to claim 1, wherein the concentration of the docosahexaenoic acid is from 50 wt. % to 98 wt. % of the total weight of fatty acid in the oil.

4. The docosahexaenoic acid containing oil according to claim 1, wherein the endothermic peak temperature, as determined by differential scanning calorimetry (DSC), is from −50° C. to 10° C.

5. The docosahexaenoic acid containing oil according to claim 1, wherein the oil is a microbial oil.

6. The docosahexaenoic acid containing oil according to claim 5, wherein the microbial oil is obtained from at least one microorganism selected from the group consisting of Opisthokonta, Archaeplastida, Excavata, SAR, a microorganism belonging to Haptophyta or Cryptophyta not classified as the aforementioned, and a bacterium.

7. The docosahexaenoic acid containing oil according to claim 5, wherein the microbial oil is obtained from a microorganism belonging to Stramenopiles.

8. The docosahexaenoic acid containing oil according to claim 5, wherein the microbial oil is obtained from a microorganism belonging to the class Labyrinthulea.

9. The docosahexaenoic acid containing oil according to claim 5, wherein the microbial oil is obtained from a Thraustochytrid microorganism.

10. The docosahexaenoic acid containing oil according to claim 5, wherein the microbial oil is obtained from a microorganism of the genus *Aurantiochytrium*.

11. The docosahexaenoic acid containing oil according to claim 5, wherein the microbial oil is of obtained from a docosahexaenoic acid producing mutant of *Aurantiochytrium limacinum*.

12. The docosahexaenoic acid containing oil according to claim 11, wherein the docosahexaenoic acid producing mutant of *Aurantiochytrium limacinum* is a NiD2 strain (accession number FERM BP-22296), a NiD3 strain (accession number FERM BP-22297), or a microbial strain having substantially the same microbiological properties as the NiD2 or NiD3 strain.

13. The docosahexaenoic acid containing oil according to claim 1, wherein the oil is a crude oil of a microbial oil.

14. The docosahexaenoic acid containing oil according to claim 1, wherein the oil is a refined oil of a microbial oil.

15. A biomass of microorganisms, the biomass comprising the docosahexaenoic acid containing oil according to claim 1.

16. The biomass according to claim 15, wherein the accumulative amount of the docosahexaenoic acid is 18 wt. % or more of the dried biomass weight per 1 liter of a culture product.

17. The biomass according to claim 15, wherein the biomass is a dried biomass.

* * * * *